United States Patent
Zhang et al.

(10) Patent No.: US 11,357,800 B2
(45) Date of Patent: Jun. 14, 2022

(54) COMPOSITIONS FOR THE TREATMENT OF NEUROPATHIC PAIN AND SENSITIZATION OF TUMORS TO CHEMOTHERAPIES

(71) Applicant: Henry Ford Health System, Detroit, MI (US)

(72) Inventors: Zhenggang Zhang, Troy, MI (US); Yi Zhang, Troy, MI (US); Michael Chopp, Southfield, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 16/322,248

(22) PCT Filed: Aug. 16, 2017

(86) PCT No.: PCT/US2017/047107
§ 371 (c)(1),
(2) Date: Jan. 31, 2019

(87) PCT Pub. No.: WO2018/035204
PCT Pub. Date: Feb. 22, 2018

(65) Prior Publication Data
US 2019/0175661 A1    Jun. 13, 2019

Related U.S. Application Data

(60) Provisional application No. 62/375,820, filed on Aug. 16, 2016.

(51) Int. Cl.
| | | |
|---|---|---|
| C12N 5/02 | (2006.01) | |
| C12N 5/071 | (2010.01) | |
| A61K 35/44 | (2015.01) | |
| C07K 14/00 | (2006.01) | |
| A61K 35/30 | (2015.01) | |
| A61P 25/02 | (2006.01) | |
| A61K 31/282 | (2006.01) | |
| A61K 31/4188 | (2006.01) | |
| A61K 35/28 | (2015.01) | |
| A61K 45/06 | (2006.01) | |
| A61K 35/12 | (2015.01) | |

(52) U.S. Cl.
CPC ............ *A61K 35/44* (2013.01); *A61K 31/282* (2013.01); *A61K 31/4188* (2013.01); *A61K 35/28* (2013.01); *A61K 35/30* (2013.01); *A61K 45/06* (2013.01); *A61P 25/02* (2018.01); *C07K 14/00* (2013.01); *A61K 2035/124* (2013.01)

(58) Field of Classification Search
CPC .... C12N 5/0618; C12N 5/069; A61K 31/282; A61K 35/44; A61P 25/02
See application file for complete search history.

(56) References Cited

U.S. PATENT DOCUMENTS

| | | |
|---|---|---|
| 2006/0035809 A1 | 2/2006 | Bolton et al. |
| 2014/0093557 A1 | 4/2014 | Zhang |
| 2015/0216899 A1 | 8/2015 | Pusic et al. |

FOREIGN PATENT DOCUMENTS

WO    WO 2013/048734 A1    4/2013

OTHER PUBLICATIONS

Riordan, Neil, 2018, US 20180036348 A1, effective filing date, Aug. 4, 2016.*
Wu et al., 2012, Aging Research reviews, vol. 11, p. 32-40.*
Agrahari et al., 2017, Expert Opinion on Drug Delivery, vol. 14, No. 10, p. 1145-1162.*
Cheng et al., 2017, Stem Cells International, vol. 2017, Article ID 6305295, 10 pages.*
Marchettini et al., 2006, Current Neuropharmacology, vol. 4, p. 175-181.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Ikehara et al., 2013, Frontier in Cell and Developmental Biology, vol. 1, Article 2, p. 1-2.*
Cooper et al., 2015, International Journal of Surgery, vol. 23, p. 211-216.*
Liu et al., 2017, Frontiers in Immunology, vol. 8, article 645, p. 1-6.*
Robbins et al., 2006, US 20060116321 A1.*
Ajit et al., Mar. 17, 2016, US 20160076098 A1.*
Wang et al., 2021, Journal of Controlled Release, vol. 329, p. 894-906.*
Zhao et al., 2020, Biomedicine and Pharmacotherapy, vol. 128, 110237, p. 1-9.*
Zheng et al., 2019, Bioconjugate Chemistry, vol. 30, p. 994-1005.*
Adams R. et al. "Axon guidance molecules in vascular patterning" Cold Spring Harb Perspectives in Biology, 2010, 2:a001875, 19 pages.
Alberts et al. "Improved Therapeutic Index of Carboplatin Plus Cyclophosphamide Versus Cisplatin Plus Cyclophosphamide: Final Report by the Southwest Oncology Group of a Phase III Randomized Trial in Stages III and IV Ovarian Cancer", Journal of Clinical Oncology, 1992, vol. 10, No. 5, p. 706-717.
Argyriou et al., "Chemotherapy-induced peripheral neurotoxicity (CIPN): An update", Critical Reviews in Oncology/ Hematology, 2012, vol. 8, p. 51-77.

(Continued)

*Primary Examiner* — Shin Lin Chen
(74) *Attorney, Agent, or Firm* — Honigman LLP; Fernando Alberdi; Jonathan P. O'Brien

(57) ABSTRACT

Without limitation, a method for preventing and/or treating neuropathic pain in a subject/patient comprising administering a therapeutically effective amount of exosomes derived and isolated from mammalian cells to the subject/patient and a method of treating cancer in a subject/patient in need thereof, comprises administering a combination comprising a therapeutically effective amount of exosomes derived and isolated from mammalian cells and a chemotherapeutic agent.

11 Claims, 15 Drawing Sheets

(56) References Cited

OTHER PUBLICATIONS

Bolen, J. B. et al. "Leukocyte Protein Tyrosine Kinases: Potential Targets for Drug Discovery", 1997, Annu. Rev. of Immunol., vol. 15, p. 371-404.
Brewer J.R. et al. "Chemotherapy-induced peripheral neuropathy: Current status and progress", Gynecologic Oncology, 2016, vol. 140, p. 176-183.
Carmeliet P. et al. "Common mechanisms of nerve and blood vessel wiring", Nature, 2005, vol. 436, p. 193-200.
Chen J. et al. "Neurorestorative therapy for stroke", Frontiers in Human Neuroscience, 2014, vol. 8, p. 382, 12 pages.
Fruhbeis C. et al. "Neurotransmitter-triggered transfer of exosomes mediates oligodendrocyte-neuron communication", PLoS Biology, 213, vol. 11, Issue 7, e1001604, 19 pages.
Gerhardt H. et al. "VEGF guides angiogenic sprouting utilizing endothelial tip cell filopodia", The Journal of Cell Biology, 2003, vol. 161, p. 1163-1177.
Goon P. et al. "Circulating endothelial cells, endothelial progenitor cells, and endothelial microparticles in cancer", Neoplasia, 2006, vol. 8, p. 79-88.
Jahroudi N. et al. "The role of endothelial cells in tumor invasion and metastasis", Journal of Neuro-Oncology, 1995, vol. 23, p. 99-108.
Kaley et al. "Journal of Clinical Oncology", British Journal of Haematology, 2009, vol. 145, p. 3-14.
Kannarkat G. et al. "Neurologic complications of chemotherapy agents", Current Opinion in Neurology, 2007, vol. 20, Issue 6, p. 719-725.
Khatua A. et al. "Exosomes packaging APOBEC3G confer human immunodeficiency virus resistance to recipient cells", Journal of Virology, 2009, vol. 83, p. 512-521.
Klagsbrun M. et al. "A role for axon guidance receptors and ligands in blood vessel development and tumor angiogenesis", Cytokine Growth Factor Reviews, 2005, vol. 16, p. 535-548.
Lombardo et al. "Discovery of N-(2-Chloro-6-methylphenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays", J. Med. Chem., 2004, vol. 47, p. 6658-6661.
Lopez-Verrilli et al. "Schwann cell-derived exosomes enhance axonal regeneration in the peripheral nervous system", GLIA, 2013, vol. 61, p. 1795-806.
Postma et al., "Long term effects of vincristine on the peripheral nervous system", Journal of Neuro-Oncology, 1993, vol. 15, p. 23-27.
Poupon L. et al. "Minimizing chemotherapy-induced peripheral neuropathy: Preclinical and clinical development of new perspectives" Expert Opinion on Drug Safety, 2015, vol. 14, p. 1269-1282.
Rosania G. et al. "Targeting hyperproliferative disorders with cyclin dependent kinase inhibitors", Expert Opinion on Therapeutic Patents, 2000, vol. 10, p. 215-230.
Saif et al., "Management of oxaliplatin-induced peripheral neuropathy" Therapeutic and Clinical Risk Management, 2005, vol. 1, No. 4, p. 249-258.
Schmoll H. et al. "Integrating oxaliplatin into the management of colorectal cancer", Oncologist, 2001, vol. 6 Suppl 4, p. 24-28.
Simons M. et al. "Exosomes—vesicular carriers for intercellular communication", Current Opinion in Cell Biology, 2009, vol. 21, p. 575-581.
Sinha S. et al. "Implications for Src Kinases in Hematopoiesis: Signal Transduction Therapeutics", J. Hematother. Stem Cell Res. 1999, vol. 8, p. 465-480.
Stoorvogel W. et al. "The biogenesis and functions of exosomes", Traffic, 2002, vol. 3, p. 321-330.
Sul J. et al. "Neurologic complications of cancer chemotherapy", Seminars in Oncologym 2006, vol. 33, p. 324-332.
Teng H. et al. "Coupling of angiogenesis and neurogenesis in cultured endothelial cells and neural progenitor cells after stroke", Journal of Cerebral Blood Flow & Metabolism, 2008, vol. 28, p. 764-771.
Thery C. et al. "Isolation and characterization of exosomes from cell culture supernatants and biological fluids", Current Protocols in Cell Biology, 2006, Chapter 3, Unit 3.22, 29 pages.
Valadi H. et al. "Exosome-mediated transfer of mrnas and micrornas is a novel mechanism of genetic exchange between cells", Nature Cell Biology, 2007, vol. 9, p. 654-659.
Wang S. et al. "Synapsin I is anoligomannose-oligomannose-carrying glycoprotein, acts as an oligomannose-binding lectin, and promotes neurite outgrmvth and neuronal survival when released via glia-derived exosomes", The Journal of Neuroscience, 2011, vol. 31, p. 7275-7290.
Weksler B. et al. "Blood-brain barrier-specific properties of a human adult brain endothelial cell line" FASEB J. 2005, vol. 19, p. 1872-1874.
Wolf et al. "Chemotherapy-induced peripheral neuropathy: Prevention and treatment strategies", European Journal of Cancer, 2008, vol. 44, p. 1507-1515.
Xin H. et al."Exosome-mediated transfer of mir-133b from multipotent mesenchymal stromal cells to neural cells contributes to neurite outgrowth" Stem Cells, 2012, vol. 30, p. 1556-1564.
Xin H. et al. "Systemic administration of exosomes released from mesenchymal stromal cells promote functional recovery and neurovascular plasticity after stroke in rats", Journal of Cerebral Blood Flow & Metabolism, 2013, vol. 33, p. 1711-1715.
Yang T. et al. "Exosome delivered anticancer drugs across the blood-brain barrier for brain cancer therapy in danio rerio", Pharm Res., 2015, vol. 32, p. 2003-2014.
Yu D. et al. "Exosomes in development, metastasis and drug resistance of breast cancer", Cancer Science, 2015, vol. 106, p. 959-964.
Zhang et al. "Exosomes in stroke pathogenesis and therapy", J Clin Invest., 2016, No. 126, vol. 4 p. 1190-1197.
Zhang J. et al. "Exosome and exosomal microma: Trafficking, sorting, and function", Genomics Proteomics Bioinformatics, 2015, vol. 13, p. 17-24.
Zhang X. et al. "Exosomes in cancer: Small particle, big player", Journal of Hematology & Oncology, 2015, vol. 8, p. 83 (13 pages).
Zhang H. et al. "Exosomes and immune surveillance of neoplastic lesions: A review", Biotechnic & Histochemistry, 212, vol. 87, p. 161-168.
Zhang J. et al. "Exosomes released from human induced pluripotent stem cells-derived mscs facilitate cutaneous wound healing by promoting collagen synthesis and angiogenesis", Journal of Translational Medicine, 2015, vol. 13, p. 49 (14 pages).
Zhang Y. Effect of exosomes derived from multipluripotent mesenchymal stromal cells on functional recovery and neurovascular plasticity in rats after traumatic brain injury. J Neurosurg., 2015, vol. 122, p. 856-867.
Christie, K. et al. "PTEN Inhibition to Facilitate Intrinsic Regenerative Outgrowth of Adult Peripheral Axons", The Journal of Neuroscience, (2010), vol. 30, No. 27, p. 9306-9315.
Katakowski, M. et al. "Exosomes as Tools to Suppress Primary Brain Tumor", Cellular and Molecular Biology, (2016), vol. 36, No. 3, p. 343-352.
Zhang, Y. et al. "Exosomes Derived from Mesenchymal Stromal Cells Promote Axonal Growth of Cortical Neurons", Molecular Neurobiology, (2017), vol. 54, p. 2659-2673.

* cited by examiner

COMPOSITIONS FOR THE TREATMENT OF NEUROPATHIC PAIN AND SENSITIZATION OF TUMORS TO CHEMOTHERAPIES

REFERENCE TO CROSS-RELATED APPLICATIONS

This application is a national stage application, filed under 35 U.S.C. 371, of International Application No. PCT/US2017/047107, filed on Aug. 16, 2017, which claims priority to, and the benefit of, U.S. Provisional Patent Application Serial No. 62/375,820, filed on Aug. 16, 2016, the disclosure of each of which is herein incorporated by reference in their entirety.

TECHNICAL FIELD

Without limitation, some embodiments comprise methods and/or compositions comprising exosomes derived from mammalian cells and use of same in the research, diagnosis, and/or treatment of sensory and motor dysfunction, abnormal sensitivity, and neurotoxicity, including peripheral neuropathy induced by chemotherapies and to sensitize tumors to chemotherapies.

BACKGROUND

Cancer is a common cause of death worldwide. An unmet need remains for new and effective methods, systems, and compositions for the treatment of cancer and its associated side effects. Chemotherapy is the use of chemical substances to treat disease and in the sense of this invention refers primarily to the use of cytotoxic drugs (called chemotherapeutic drugs) to treat cancer. Chemotherapy in cancer consists of a personalized combination of potent chemotherapy drugs, designed to slow rapid cancer tumor growth, shrink tumors, kill cancer cells, and prevent the spread of cancer. The chemotherapeutic drugs prevent cells from replicating in the typical, out-of-control manner in which cancer cells divide. Chemotherapy-induced peripheral neuropathy (CIPN) is one of the most common, serious side effects that can lead to dose reductions or early discontinuation of chemotherapy, reducing the efficacy of cancer treatments. It can cause debilitating symptoms and also significantly impacts the patient's quality of life. An estimated 30 to 40 percent of cancer patients treated with chemotherapy experience CIPN.

The peripheral nervous system (PNS) consists of sensory neurons running from stimulus receptors that inform the central nervous system (CNS) of the stimuli, and motor neurons running from the spinal cord to the effectors that take action. In CIPN, an anticancer drug could impair both sensory and motor functions. "Neuropathic pain" is defined by the International Association For The Study Of Pain (IASP) as "pain initiated or caused by a primary lesion or dysfunction in the nervous system" (IASP, Classification of chronic pain, $2^{nd}$ Edition, IASP Press (2002), p. 210). For the purpose of this invention included under this heading or to be treated as synonymous is "Neurogenic Pain" which is defined by the IASP as "pain initiated or caused by a primary lesion, dysfunction or transitory perturbation in the peripheral or central nervous system". In regards to this invention, the neuropathic pain treated according to this invention is restricted to the neuropathic pain resulting from chemotherapy, meaning being caused by the administration and use of a chemotherapeutic drug in chemotherapy. The most likely cause of this is neurotoxicity of the chemotherapeutic drug, especially peripheral neurotoxicity.

Patients will often experience symptoms usually starting in the hands and/or feet and creep up the arms and legs. Patients may in addition or alternatively experience symptoms ranging from a shooting and/or burning pain or sensitivity to temperature, for example, include sharp, stabbing pain. CIPN symptoms can also include hearing loss, blurred vision and change in taste. CIPN can make it difficult to perform normal day-to-day tasks like buttoning a shirt, sorting coins in a purse, or walking. In addition, the motor neuron dysfunction can manifest as cramps, difficulty with fine motor activities (e.g. writing or dialing a phone), gait disturbances, paralysis, spasms, tremors and weakness.

Peripheral neuropathy is a common complication of several classes of chemotherapeutic agents including taxanes (paclitaxel and docetaxel), platinum-based compounds (carboplatin, cisplatin, and oxaliplatin), and vinca alkaloids (vincristine and vinblastine). Because these agents are used to treat several prevalent cancers, chemotherapy-induced peripheral neuropathy (CIPN) is common in patients treated with chemotherapy. CIPN is manifested by the development of paresthesias, dysesthesias, loss of joint and vibration sense, and loss of deep tendon reflexes. The onset of symptomatic CIPN usually leads to reductions in dose(s) and/or interruptions of therapy, which can negatively impact cancer-related outcomes.

There are few effective pharmacological options to treat symptoms due to CIPN. Analgesics (i.e., opioids and non-steroidal anti-inflammatory agents) are only modestly effective in treating symptoms from neuropathy. Tricyclic antidepressants (e.g., nortriptyline and amitriptyline) have been suggested as therapeutic options for neuropathy; however, there are few data to support their use in CIPN. One randomized trial evaluated nortriptyline for therapy of CIPN symptoms; this agent was found to be ineffective. Compared to other neuropathies or neuropathic pain syndromes, there is a resemblance to diabetic neuropathy with similar glove and stocking distribution and other symptoms, such as pain, paresthesias, and dysesthesias. However, treatments for diabetic neuropathies are not necessarily helpful for preventing or treating neuropathies associated with chemotherapy.

Given the prevalence of CIPN, and that it can be dose-limiting for several cytotoxic drugs, symptom control studies have been conducted looking at ways to prevent or alleviate established CIPN. The identification of alternate treatment strategies would be a welcome development for patients afflicted with CIPN. Outside of clinical trials, CIPN symptoms are commonly managed in a manner similar to other types of nerve pain, that is, with a combination of physical therapy, complementary therapies such as massage and acupuncture, and medications that can include steroids, antidepressants, anti-epileptic drugs, and opioids for severe pain. But these therapies have not demonstrated true efficacy for CIPN, and virtually all of the drugs to treat peripheral neuropathy carry side effects of their own.

The actual causes of CIPN, on the cellular and tissue level, is still largely a matter of speculation. Oxidative stress may play a key role in CIPN. It was found that antioxidant machinery (e.g. plasma glutathione (GSH) and α- and γ-tocopherol concentrations) of cancer patients with chemotherapy decreased and the GSH redox state became more oxidized. In a rat model of painful oxaliplatin-induced neuropathy, oxidative stress was found to be an important component that mediates pain. In the plasma of oxaliplatin-treated rats, the increase in carbonylated protein and thiobarbituric acid reactive substances in the sciatic nerve and the spinal cord indicated the resultant protein oxidation and lipoperoxidation in these locations, respectively. Oxidative imbalance manifests itself as a mediator of inflammatory pain as well. Use of the anticancer drug cisplatin results in severe cell death of sensory neurons derived from dorsal root ganglia following increase in oxidative stress. Oxidative stress is also found to impair the autonomic nervous system and manifests itself in symptoms such as hearing loss. The results from antioxidants also support a key role of oxidative stress in mediating CIPN. The antineuropathic effect of antioxidant silibinin or α-tocopherol shows as about 50% oxaliplatin-induced behavioral alterations. Administration of anticancer drug bortezomib or oxaliplatin, which elicits TRPA1-dependent hypersensitivity, produced a rapid, transient increase in plasma of carboxy-methyllysine, a by-product of oxidative stress. Short-term systemic treatment with either antioxidants could completely prevent hypersensitivity if administered before the cytotoxic drug. The findings highlight a key role for early activation/sensitization of TRPA1 by oxidative stress by-products in producing CIPN. For preventing the onset of CIPN, further clinical testing of many antioxidative stress agents, such as glutathione, acetyl-L-carnitine and α-lipoic acid has been suggested.

Another mechanism underlying CIPN is excitotoxicity where increased release of glutamate forces N-methyl D-aspartate (NMDA) receptors to remain open, allowing increased calcium flux into neurons, resulting in overexcitation and eventually neuronal rupture. The end result of this process is pain without a painful stimulus, also known as neuropathic pain. N-Acetyl-aspartyl-glutamate (NAAG) is an abundant neuropeptide widely distributed in the central and peripheral nervous system which is physiologically hydrolyzed by the enzyme glutamate carboxypeptidase into N-Acetyl-aspartyl (NAA) and glutamate. Glutamate carboxypeptidase inhibition could reduce the severity of chemotherapy-induced peripheral neurotoxicity in rat.

As there are no proven treatments, there is a need for new compositions and methods to properly treat neurotoxicity, for example, peripheral neuropathy, such as chemotherapy-induced peripheral neuropathy or radiation-induced peripheral neuropathy. The present invention provides compositions and methods for the treatment of sensory and motor dysfunction, abnormal sensitivity, and neurotoxicity, including peripheral neuropathy induced by chemotherapies and radiation therapies, for example, CIPN and also providing the unexpected effect of further sensitizing tumor cells to chemotherapeutics.

BRIEF DESCRIPTION OF THE DRAWINGS

Some embodiments will now be described, by way of example only and without waiver or disclaimer of other embodiments or subject matter, with reference to the accompanying drawings, in which:

DETAILED DESCRIPTION

Figure 1:
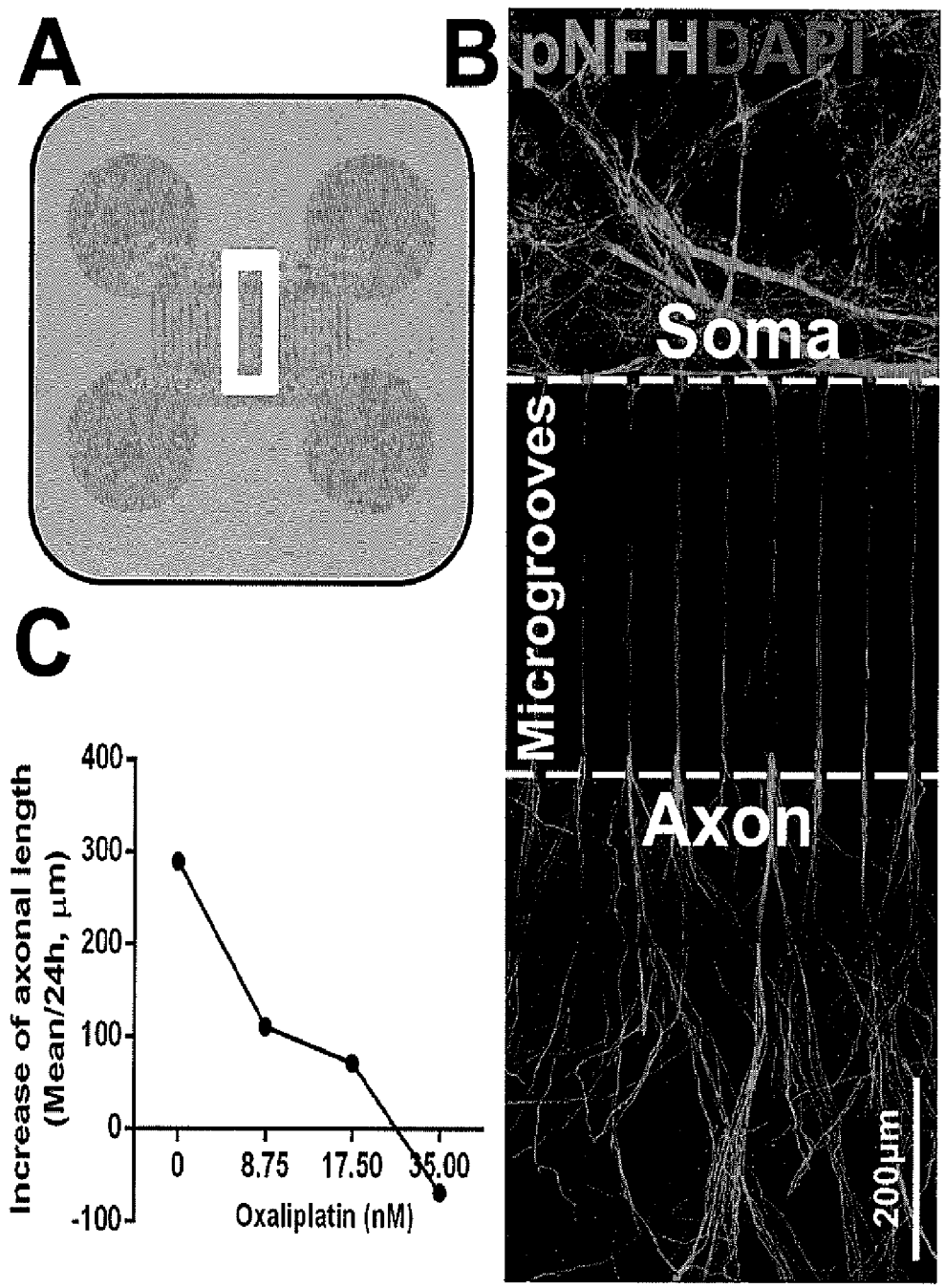
FIG. 1A is a data representation showing axonal growth and the effect of oxaliplatin on the axonal growth. The schematic illustration of a microfluidic device (A).
FIG. 1B Photomicrographs of an enlarged square area (B) in FIG. 1A of a microfluidic culture device show the cell body (Soma) and axonal (Axon) compartments. Note, only distal axons of DRG neurons grow into the axonal compartment from their parental cell bodies within the cell body compartment (B).
FIG. 1C shows quantitative data of axonal growth of DRG neurons under different concentrations of Oxaliplatin (0, 8.75, 17.50 and 35.00 nM) when Oxaliplatin was added into the axonal compartment for 24 h.

Without limitation to only those embodiments expressly disclosed herein, and without waiver or disclaimer of any embodiments or subject matter, some embodiments comprise methods, systems and/or compositions comprised of exosomes derived from mammalian cells, for example, stem cells, mesenchymal stromal cells, umbilical cord cells, endothelial cells, (for example, cerebral endothelial cells, brain microvascular endothelial cells, Primary Human Brain Microvascular Endothelial Cells (ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes. As used herein, stem cells, for example, from a human mammalian subject can include, without limitation, a progenitor cell, a pluripotent stem cell, an induced pluripotent stem cell, a hair follicle stem cell, a hematopoietic stem cell, a very small embryonic like stem cell, a mesenchymal stem cell, an endometrial regenerative cell (ERC), or a progenitor cell. In various embodiments, the cell population includes mesenchymal stem cells, and mesenchymal stromal cells, cerebral endothelial cells (CECs) and their use in research, diagnosis, or treatment of conditions, diseases, or injuries of mammalian subjects, including but not limited to, the treatment of cancers.

In some embodiments, the inventors have discovered unexpectedly that, in accordance with some non-limiting embodiments, patients with cancer can be treated with therapeutically effective amounts of exosomes, derived from mammalian cells, for example, autologous or allogeneic cells, for example, human cells capable of producing such exosomes, and compositions containing the contents of such exosomes, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes, to prevent and/or treat neurological vascular and cellular toxicity (for example, toxicity to Schwann cells) that may lead to neurotoxicity, for example peripheral neuropathy (herein referred to as chemotherapy induced peripheral neuropathy (CIPN), by administering said exosomes, before, during or after the administration of a chemotherapeutic to treat the patient's cancer and provide relief against the adverse neurotoxic or CIPN side-effect associated with chemotherapeutic administration.

In another non-limiting embodiment, the present invention is directed to the treatment of a cancer patient. The method includes administering a therapeutically effective amount of exosomes derived from stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes, before, during or after the administration of one or more chemotherapeutic agents in a therapeutically effective amount during the course of chemotherapy to treat the patient's cancer. In some illustrative embodiments, the exosomes are derived from stem cells, mesenchymal stromal cells or endothelial cells, for example, cerebral endothelial cells (CECs), brain microvascular endothelial cells (BMVEC), Primary Human Brain Microvascular Endothelial Cells (PHBMVEC) (for example, ACBRI 376), endothelial progenitor cells, AG-133/CD-133+ cells and the like.

The exosomes may be autologous or allogeneic. An "effective amount" or a "therapeutically effective amount" of a composition containing exosomes with or without a chemotherapeutic agent, e.g., a pharmaceutical formulation, refers to an amount effective, at dosages and for periods of time necessary, to achieve the desired therapeutic or prophylactic result.

Treatment with platinum-based anticancer agents are commonly used to treat lung, colorectal, ovarian, breast, head/neck, and genitourinary cancers. However, peripheral neuropathy is a common adverse effect of the chemotherapy, which mainly affects dorsal root ganglia (DRG) neurons. Mechanisms that underlie peripheral neuropathy have not been fully understood and there are currently no effective treatments to reduce chemotherapy-induced peripheral neuropathy. Exosomes, the extracellular vesicles released by living cells, play pivotal roles in cell-cell communication by transferring their cargo, proteins, lipids and genetic materials, to recipient cells. The present invention provides methods for treating chemotherapy induced neurotoxicity including neuropathy, by administering a therapeutically effective dose of exosomes derived and isolated from CECs to a patient or subject with said neurotoxicity and/or neuropathy.

The terms "subject" and "individual" and "patient" are used interchangeably herein, and refer to an animal, for example a mammal, for example, a human or non-human mammal, to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates, (particularly higher primates and monkeys), sheep, dogs, rodents (e.g. mouse or rat), guinea pigs, goats, pigs, cats, rabbits, cows, and non-mammals such as chickens, amphibians, reptiles etc. In one embodiment, the subject is human. In another embodiment, the subject is an experimental animal or animal substitute as a disease model. Non-human mammals include mammals such as non-human primates, (particularly higher primates and monkeys), sheep, dogs, rodents (e.g. mouse or rat), guinea pigs, goats, pigs, cats, rabbits and cows. In some aspects, the non-human animal is a companion animal such as a dog or a cat.

Exosome Compositions and Formulations

In some embodiments, without limitation, the methods described herein can utilize compositions and/or formulations containing exosomes derived from a variety of exosome producing mammalian cells. In various embodiments, compositions of the present disclosure may contain exosomes or exosome constituents, i.e. exosome contents derived from exosomes harvested or isolated from stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes. In some preferred embodiments, the exosomes useful in the compositions and methods of the present disclosure are derived from stem cells, mesenchymal stromal cells or endothelial cells, for example, cerebral endothelial cells (CECs), brain microvascular endothelial cells (BMVEC), Primary Human Brain Microvascular Endothelial Cells (PHBMVEC) (for example, ACBRI 376), endothelial progenitor cells, AG-133/CD-133+ cells and the like. Exosomes useful in the present methods and compositions may contain at least one of the following exosomal markers: Alix and CD63. CEC derived exosomes can be isolated from primary tissue, such as brain endothelial cells, from human tissue cultured cells, for example, brain microvascular endothelial cells (BMVECs), or Primary Human Brain Microvascular Endothelial Cells (ACBRI 376) commercially available from Cell Systems Corporation (CSC) Kirkland, Wash., USA. CEC derived exosomes are released from cultured brain endothelial cells either through exocytosis of multivesicular bodies (MVBs) forming 50-150 nm-diameter exosomes. In some embodiments, immortalized human brain microvascular endothelial cells, HCMEC/D3 (as described in Weksler B B, Subileau E A, Perriere N, Charneau P, Holloway K, Leveque M, Tricoire-Leignel H, Nicotra A, Bourdoulous S, Turowski P, Male DK, Roux F, Greenwood J, Romero I A, Couraud P O: Blood-brain barrier-specific properties of a human adult brain endothelial cell line. FASEB J. 2005, 19: 1872-1874, the disclosure of which is incorporated herein by reference in its entirety) can be used as a source of CEC derived exosomes. The HCMEC/D3 cells are grown in a humidified atmosphere of 5% $CO_2$/95% $O_2$ at 37° C. in EBM-2 basal medium (Lonza, Walkersville, Md., USA), supplemented with one quarter of a SingleQuot kit (Lonza) and 2% fetal bovine serum in flasks coated with 100 μg/ml rat tail collagen type I (BD Canada, Mississauga, ON, Canada), diluted in 20 mM acetic acid. Cells from passages 20 to 40 can be used for harvesting CEC-derived exosomes. Exosome production can be achieved in serum-free conditions since serum has endogenous exosomes and serum molecules can non-specifically bind to CEC derived exosomes. To prepare for CEC derived exosome isolation, cells are grown until confluence, washed at least three times with a buffered-saline solution and then incubated in serum-free medium for at least 1 day to obtain a sufficient amount of CEC derived exosomes.

Isolation of CEC Derived Exosomes from Human Brain Endothelial Cells (HBEC)

An exemplary exosome isolation method can be adapted from Thery C, Amigorena S, Raposo G, Clayton A: "Isolation and characterization of exosomes from cell culture supernatants and biological fluids". Curr. Protoc. Cell Biol. 2006 April; Chapter 3: Unit 3.22, the disclosure of which is incorporated herein by reference in its entirety. Typically, 100 mL of cultured media is used by pooling from multiple dishes. The media is centrifuged at 300×g for 10 min at 4°

C. to remove any intact cells, followed by a 2,000×g spin for 20 min at 4° C. to remove dead cells and finally a 10,000×g spin for 30 min at 4° C. to remove cell debris. The media is then transferred to ultracentrifuge tubes and centrifuged at 100,000×g for at least 60 min at 4° C. in Optima TLX ultracentrifuge with 60 Ti rotor (Beckman Coulter, Mississauga, Canada). The supernatant containing exosome-free media is removed and the pellets containing exosomes plus proteins from media are resuspended in PBS. The suspension is centrifuged at 100,000×g for at least 60 min at 4° C. to collect final exosome pellets. The exosome pellet is then resuspended in an appropriate excipient or diluent in a desired volume to attain a specific concentration of exosomes per mL.

Methods of Preventing and/or Treating Neurotoxicity During Chemotherapy and Radiation Therapy In some non-limiting embodiments, the present invention provides a method for treating neurotoxicity in a subject in need thereof. In some embodiments, the neurotoxicity may be caused by the administration of one or more chemotherapeutic agents delivered during a course or multiple courses of chemotherapy, or after administration of one or more courses of radiation therapy for the treatment of a cancer in a subject. In some non-limiting embodiments the present invention provides a method for treating neurotoxicity caused by the administration of drug therapies, and organ transplants. Neurotoxicity occurs when the exposure to chemotherapeutic agents and radiation treatments (neurotoxicants), drug therapies, and organ transplants alters the normal activity of the nervous system (central nervous system and peripheral nervous system). While not wishing to be bound by any theory, it is believed that continued exposure to neurotoxicants such as chemotherapeutic agents and radiation treatments can eventually disrupt or even kill neurons. Symptoms may appear immediately after exposure or be delayed. They may include limb weakness or numbness; pain; loss of memory, vision, and/or intellect; headache; cognitive and behavioral problems; and sexual dysfunction. One manifestation of neurotoxicity includes peripheral neuropathy. Peripheral neuropathy describes damage to the peripheral nervous system, which transmits information from the brain and spinal cord to every other part of the body.

More than 100 types of peripheral neuropathy have been identified, each with its own characteristic set of symptoms, pattern of development, and prognosis. Impaired function and symptoms depend on the type of nerves: motor, sensory, or autonomic, that are damaged. Some people may experience sensory and/or motor dysfunction, including abnormal sensitivity. Other symptoms may include: temporary numbness, tingling, pricking sensations, sensitivity to touch, or muscle weakness. Others may suffer more extreme symptoms, including pain for example, burning pain (especially at night), muscle wasting, paralysis, or organ or gland dysfunction.

In some embodiments, patients with cancer can be treated with therapeutically effective amounts of mammalian cell derived exosomes, for example, stem cell, mesenchymal stromal cell and endothelial cell derived exosomes, to prevent and/or treat neurotoxicity, for example peripheral neuropathy (herein referred to illustratively as chemotherapy induced peripheral neuropathy (CIPN)), by administering said mammalian cell derived exosomes, before, during or after the administration of a chemotherapeutic or radiation treatment used to treat the patient's cancer and provide relief against the adverse neurotoxic or CIPN side-effects associated with chemotherapeutic and/or radiation therapy administration. In some embodiments, the cells operable to produce exosomes, or the exosomes themselves, may be subjected to ischemia or other forms of physiological stress prior to their use in the compositions and formulations disclosed herein.

In some embodiments, therapeutically effective amounts of exosomes may be administered to a patient before, during or after the administration of one or more chemotherapeutic agents or radiation therapy to reduce the symptomatology and pathological effects associated with a chemotherapy or radiation induced neurotoxicity, for example, neuropathy, for example, peripheral neuropathy.

A "chemotherapeutic agent" as used herein generally refers to a chemical compound useful in the treatment of a hyper-proliferative disease and disorder and cancer. Examples of chemotherapeutic agents include alkylating agents, anti-hormonal agents or endocrine therapeutics, antibiotics, anti-metabolites, folic acid analogues, pyrimidine analogs, androgens, anti-adrenals, maytansinoids, taxoids, platinum agents, vincas, which prevent tubulin polymerization from forming microtubules, topoisomerase I & II inhibitors, PARP inhibitors, retinoids, bisphosphonates, antisense oligonucleotides, vaccine and gene therapy vaccines, COX-2 inhibitors, proteosome inhibitors, Bcl-2 inhibitors, EGFR inhibitors, VEGFR inhibitors, tyrosine kinase inhibitors, serine-threonine kinase inhibitors, and farnesyltransferase inhibitors. Chemotherapeutic agents as defined herein also include chemical compounds which act to regulate, reduce, block, or inhibit the effects of hormones that can promote the growth of cancer. They may be hormones themselves, including, but not limited to: anti-estrogens with mixed agonist/antagonist profile.

Based on the key roles of excito-neurotoxicity and oxidative stress in chemotherapy-induced peripheral neuropathy (CIPN), administration of any one or more of the mammalian cell derived exosomes containing compositions of the present invention, when dosed in therapeutically effective amounts to a cancer patient having been administered a symptom associated with or caused by neurotoxicity, for example, chemotherapy-induced peripheral neuropathy that is not only caused with antimetabolites (cytarabine, gludarabine, fluorouracil, mercaptopurine, methotrexate, thioguanine, gemcitabine, hydroxyurea), mitotic inhibitors (vincristine, vinblastine, vinorelbine), topoisomerase inhibitors (topotecan, irinotecan), paclitaxel, docetaxel and asparaginase, but also with alkylating agents (busulfan, carmustine, lomustine, chlorambucil, cyclophosphamide, cisplatin, carboplatin, oxaliplatin, ifosamide, mechlorethamine, melphalan, thiotepa, dacarbazine, procarbazine), antitumor antibiotics (bleomycin, dactinomycin, daunorubicin, doxorubicin, idarubicin, mitomycin, mitoxantrone, plicamycin), topoisomerase II inhibitor (etoposide, teniposide), and radiation therapy. In addition, the exosome containing composition of the present invention should inhibit chemotherapy-induced peripheral neuropathy caused by an anticancer drug, such as ixabepilone, arsenic trioxide, etoposide, hexamethylmelamine, ifosfamide, methotrexate, procarbazine, epothilones, bortezomib, lenolidamide thalidomide, cisplatin, carboplatin, oxaliplatin, vincristine, vinblastine, paclitaxel, and docetaxel.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

The terms "cell proliferative disorder" and "proliferative disorder" refer to disorders that are associated with some degree of abnormal cell proliferation. In one embodiment, the cell proliferative disorder is cancer.

The terms "cancer" and "cancerous" refer to or describe the physiological condition in mammals that is typically characterized by unregulated cell growth/proliferation, and includes all types of cancer, neoplasm or malignant tumors found in mammals, including humans, including leukemia, carcinomas and sarcomas. Exemplary cancers that may be treated with a composition or formulation containing exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes, pharmaceutical compositions containing the above referenced exosomes or their internal constituents, and one or more chemotherapeutic agents, as described herein, include breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme (GBM), glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes and a chemotherapeutic agent, or methods provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes and a chemotherapeutic agent, or methods provided herein include: chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes and a chemotherapeutic agent, or methods provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes and a chemotherapeutic agent, or methods provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In various embodiments, the exosomes containing compositions described herein interfere with the neurotoxic side effects associated with chemotherapeutic agent or radiation therapy administration. In accordance with some embodiments, there is a high likelihood that the duration of therapy comprising exosome administration would be relatively brief and with a high probability of success. Prophylactic exosome administration of some embodiments may greatly reduce the incidence of damage associated with many forms of chemotherapeutic and/or radiation induced neurotoxicity.

Any appropriate routes of exosome administration known to those of ordinary skill in the art may comprise embodiments of the invention.

Exosomes derived from mammalian cells, for example, stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes, or their internal components thereof, can be administered and dosed in accordance with good medical practice, taking into account the clinical condition of the individual patient, the site and method of administration, scheduling of administration, patient age, sex, body weight and other factors known to medical practitioners.

The "pharmaceutically effective amount" for purposes herein is thus determined by such considerations as are known in the art, and may also include "therapeutically effective amounts" (also used synonymously) which is broadly used herein to mean an amount of any exosomes, that when administered to a patient, ameliorates, diminishes, improves or prevents a symptom of neurotoxicity, for example, a neuropathy, for example, peripheral neuropathy, for example, CIPN. The amount of the exosomes described herein or their internal components which constitutes a "therapeutically effective amount" will vary depending on the exosome density, the disease state and its severity, the age of the patient to be treated, and the like. preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of exosomes and/or the chemotherapeutic agent in the exemplified compositions, and formulations, whether pharmaceutically acceptable or not, may vary according to factors such as the type of disease, state, age, sex, and weight of the individual. Dosage regimens may be adjusted to provide the optimum therapeutic response. For example, a single bolus of exosomes (or compositions containing the contents of said exosomes) may be administered, several divided doses may be administered over time or the dose may be proportionally reduced or increased as indicated by the exigencies of the therapeutic situation. It is especially advantageous to formulate parenteral compositions (for example by intravenous (IV), intraperitoneal (IP), intranasal (IN), subcutaneous (S.C.) or other known routes for delivery of cells or components thereof) in a dosage unit form for ease of administration and uniformity of dosage. Dosage unit form as used herein refers to physically discrete units suited as unitary dosages for the mammalian subjects to be treated; each unit containing a predetermined quantity of active compound (e.g., exosomes with or without a chemotherapeutic agent) calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

"Patient" or "Subject" are used interchangeably and for the purposes of the present invention includes humans and other animals, particularly mammals, and other organisms. Thus the methods are applicable to both human therapy and veterinary applications. More specifically, the patient is a mammal, and in some embodiments, the patient or subject is human.

"Treating" or "treatment" or "to treat" in the context of this specification means administration of an exosome containing composition or formulation according to the invention to reduce prevent, ameliorate or eliminate one or more symptoms associated with neuropathy, for example, peripheral neuropathy, which may include: neuropathic pain, hyperalgesia and/or allodynia. Furthermore, the terms "to treat" or "treatment" according to this invention include the treatment of symptoms of neuropathic pain, hyperalgesia and/or allodynia, the prevention or the prophylaxis of the symptoms of neuropathic pain, hyperalgesia and/or allodynia, the prevention or prophylaxis causing the symptoms of neuropathic pain, hyperalgesia and/or allodynia, as well as the prevention or the prophylaxis of the consequences causing the symptoms.

"Prevent" or "preventing" or "prevention" refer to prevention or delay of the onset of the neurotoxic disorder or symptom, and/or a decrease in the level of pain in a subject relative to the symptom of the neurotoxic disorder or symptom level of pain that would develop in the absence of the methods of the invention. The prevention can be complete, e.g., the total absence of pain in a subject. The prevention can also be partial, such that the occurrence of pain in a subject is less than that which would have occurred without the present invention.

In some embodiments, the methods of the present invention provide prophylactic and therapeutically effective treatments for neurotoxicity in a patient in need thereof. In some embodiments, such methods comprises administering a therapeutically effective amount of mammalian exosomes to the patient or subject diagnosed with neurotoxicity, or experiencing one or more symptoms of neurotoxicity. For example, neurotoxicity symptoms may include: sensory and/or motor dysfunction, abnormal sensitivity, temporary numbness, tingling, pricking sensations, sensitivity to touch, muscle weakness, pain, muscle wasting, paralysis, or organ or gland dysfunction. In some embodiments, the methods of the present invention may be used to prevent or treat a condition selected from: chemotherapy-induced neuropathy, cancer-related neuropathy, HIV-related peripheral neuropathy, post-herpetic neuralgia, diabetic neuropathy, peripheral neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post-surgical pain syndrome, post mastectomy syndrome, post thoracotomy syndrome, phantom pain, nerve root avulsion, post radiation neuropathy, repetitive movement nerve injury, repetitive stress injury, post injury neuropathy, or combinations thereof.

In a further embodiment of the use according to the invention comprises preventing and/or treating neuropathic pain, which may include peripheral neuropathic pain or peripheral neurogenic pain.

In one embodiment of the invention, an exosome containing composition or formulation as described herein is used to treat or prevent pain in a subject. Pain can be defined as any type of nociceptive pain, somatic pain, visceral pain, or neuropathic pain. In one embodiment, the pain can be due to a neuropathy, e.g., neuropathic pain. The neuropathy can be any form of neuropathy. In some embodiments, the neuropathy is selected from the group consisting of chemotherapy-induced neuropathy, cancer-related neuropathy, HIV-related peripheral neuropathy, post-herpetic neuralgia, diabetic neuropathy, sciatica, fibromyalgia, chronic fatigue syndrome pain, multiple sclerosis pain, complex regional pain syndrome type I, complex regional pain syndrome type II, central pain syndrome, painful traumatic mononeuropathy, post-surgical pain syndrome, post mastectomy syndrome, post thoracotomy syndrome, phantom pain, nerve root avulsion, post radiation neuropathy, repetitive movement nerve injury, repetitive stress injury, and post injury neuropathy. In one embodiment, the pain that is treated or prevented includes nociceptive pain. In another embodiment, the pain that is treated or prevented excludes nociceptive pain.

In an additional embodiment, where the composition containing exosomes, or their constituents of the invention is used to treat or prevent a chemotherapy-induced neuropathy (CIPN) in a subject, the CIPN may be a chemotherapy-induced peripheral neuropathy (CIPN). CIPN is attributable to a broad variety of antineoplastic agents. CIPN-inducing agents generally come from six principal drug classes including platinum agents, taxanes, vinca alkaloids, boronic acid derivatives, phthaloyl derivatives and epothilones are an illustrative list of known chemotherapeutics that cause neurotoxicity, and in particular peripheral neuropathy.

CIPN can manifest as any one of at least twenty distinct symptoms affecting sensory, motor, and autonomic systems. Sensory symptoms include pain, tingling, numbness, instability when standing or walking, problems distinguishing temperature, and hearing problems. Motor symptoms include cramps, difficulty writing, difficulty manipulating small objects, and weakness. Autonomic symptoms include vision changes, dizziness after changing position, and erection disorders. Commonly used indices for the measurement of CIPN include the National Cancer Institute-Common Toxicity Criteria (NCI-CTC) score (see, Argyriou et al., Crit. Rev Oncol/Hematol 2012; 85:51-77) and the Numeric Rating Scale (NRS), a method for assessing pain that is well-known to those of ordinary skill in the art.

In a particular embodiment, the CIPN treated by the exosomes of the present disclosure is painful chemotherapy-induced peripheral neuropathy (painful CIPN). Painful CIPN can be a debilitating condition that currently has no validated preventative or treatment (see, Wolf et al., Eur J Cancer 2008; 44:1507-1515; Kaley and DeAngelis, Brit J Haematol 2009; 145:3-14). In further embodiments, the painful CIPN treated by the exosomes of the invention can be either painful acute chemotherapy-induced peripheral neuropathy (painful ACIPN) or painful chronic chemotherapy-induced peripheral neuropathy (painful CCIPN).

Painful ACIPN commonly occurs during administration of a variety of chemotherapeutic agents and resolves spontaneously within days or up to about 12 weeks after cessation of chemotherapy. Painful ACIPN can be caused by commonly used chemotherapeutic agents including carboplatin, vincristine, vinblastine, and ixabepalone. Painful ACIPN induced by these agents has been demonstrated to be reversible when drug administration ends (see, Alberts et al., J Clin Oncol 1992; 10:706-717; Postma et al., J Neuro-Oncol. 1993; 15:23-27; Argyriou et al., Crit. Rev Oncol/Hematol 2012; 85:51-77; Kannarkat et al., Curr Opin Neurol. 2007; 20:719-725).

By contrast, painful CCIPN is defined as neuropathic pain associated with the administration of chemotherapeutic agents which fails to resolve by about twelve weeks after cessation of the last cycle of chemotherapy. Painful CCIPN commonly results from the administration of any one of six important chemotherapeutic agents that are widely used in the treatment of a variety of cancers. These chemotherapeutic agents include cisplatin, oxaliplatin, paclitaxel, docetaxel, bortezomib, and thalidomide. Painful CCIPN can be caused by these chemotherapeutic agents alone or a combination of agents.

According to the IASP "peripheral neuropathic pain" is defined as "a pain initiated or caused by a primary lesion or dysfunction in the peripheral nervous system" and "peripheral neurogenic pain" is defined as "a pain initiated or caused by a primary lesion, dysfunction or transitory perturbation in the peripheral nervous system" (IASP, Classification of chronic pain, $2^{nd}$ Edition, IASP Press (2002), p. 213).

In another embodiment of the use according to the invention the neuropathic pain is allodynia. According to the IASP "allodynia" is defined as "a pain due to a stimulus which does not normally provoke pain" (IASP, Classification of chronic pain, $2^{nd}$ Edition, IASP Press (2002), p. 210).

In another embodiment of the use according to the invention the neuropathic pain is causalgia. According to the IASP "causalgia" is defined as "a syndrome of sustained burning pain, allodynia and hyperpathia after a traumatic nerve lesion, often combined with vasomotor and sudomotor dysfunction and later trophic changes" (IASP, Classification of chronic pain, $2^{nd}$ Edition, IASP Press (2002), p. 210).

In another embodiment of the use according to the invention the neuropathic pain is hyperalgesia. According to the IASP "hyperalgesia" is defined as "an increased response to a stimulus which is normally painful (IASP, Classification of chronic pain, $2^{nd}$ Edition, IASP Press (2002), p. 211).

In another embodiment of the use according to the invention the neuropathic pain is hyperesthesia. According to the IASP "hyperesthesia" is defined as "increased sensitivity to stimulation, excluding the senses" (IASP, Classification of chronic pain, $2^{nd}$ Edition, IASP Press (2002), p. 211).

In another embodiment of the use according to the invention the neuropathic pain is hyperpathia. According to the IASP "hyperpathia" is defined as "a painful syndrome characterized by an abnormally painful reaction to a stimulus, especially a repetitive stimulus, as well as an increased threshold" (IASP, Classification of chronic pain, $2^{nd}$ Edition, IASP Press (2002), p. 212).

In another preferred embodiment of the use according to the invention the neuropathic pain is neuralgia. According to the IASP "neuralgia" is defined as "Pain in the distribution of a nerve or nerves" (IASP, Classification of chronic pain, $2^{nd}$ Edition, IASP Press (2002), p. 212).

In another embodiment of the use according to the invention the neuropathic pain is neuritis. According to the IASP "neuritis" is defined as "Inflammation of a nerve or nerves" (IASP, Classification of chronic pain, $2^{nd}$ Edition, IASP Press (2002), p. 212).

In another embodiment of the use according to the invention the neuropathic pain is orofacial pain.

A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, mTOR inhibitors, and kinase inhibitors. Chemotherapeutic agents include compounds used in "targeted therapy" and non-targeted conventional chemotherapy.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance, and bioavailability.

In various embodiments, therapeutically effective compositions or formulations containing exosomes (or their internal components) useful in the prevention and/or treatment of neurotoxicity, including peripheral neuropathy, for example, a mammalian cell derived exosome containing composition or formulation can be administered before, after or concurrently with the administration of a chemotherapeutic agent or agents, or before, after or concurrently with the administration of a radiation therapy. "Concurrently" means sufficiently close in time to produce a combined effect (that is, concurrently can be simultaneously, or it can be two or more events occurring within a short time period before or after each other). In some embodiments, the administration of two or more agents in a combination "concurrently" means that the two agents are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

In some embodiments, therapeutically effective compositions or formulations of the present invention may contain whole mammalian cell derived exosome, i.e. whole particles, partially disrupted mammalian cell derived exosome, or mammalian cell derived exosome contents, i.e. the internal constituents of mammalian cell derived exosome minus the exosome membrane. Accordingly, the invention further provides a pharmaceutical composition comprising mammalian cell derived exosome of the invention. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing mammalian cell derived exosome of the invention with one or more pharmaceutically acceptable carriers, diluents and/or excipients.

In certain embodiments, the mammalian cell derived exosome containing compositions or formulations of the invention can contain further additives including, but not limited to, pH-adjusting additives, osmolarity adjusters, tonicity adjusters, anti-oxidants, reducing agents, and preservatives. Useful pH-adjusting agents include acids, such as hydrochloric acid, bases or buffers, such as sodium lactate, sodium acetate, sodium phosphate, sodium citrate, sodium borate, or sodium gluconate. Further, the compositions of the invention can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., .alpha.-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

In another embodiment of the invention, CEC derived exosomes or pharmaceutically acceptable compositions containing CEC derived exosomes described herein is used to treat or prevent neurotoxicity in a subject. The neurotoxicity can be any type of neurotoxicity including, but not limited to, peripheral neuropathy, hearing loss, allodynia, pain, numbness, tingling, burning, muscle weakness, and dizziness.

In another embodiment of the invention, mammalian cell derived exosomes described herein are administered to the subject as needed to treat or prevent neurotoxicity. The mammalian cell derived exosome can be administered continuously or intermittently. In one embodiment, the mammalian cell derived exosome containing composition or formulation is administered to the subject more than once a day or once every 1, 2, 3, 4, 5, 6, or 7 days. In another embodiment, the mammalian cell derived exosome containing composition or formulation is administered to the subject no more than once a week, e.g., no more than once every two weeks, once a month, once every two months, once every three months, once every four months, once every five months, once every six months, or longer. In a further embodiment, the mammalian cell derived exosome containing composition or formulation is administered using two or more different schedules, e.g., more frequently initially (for example to build up to a certain level, e.g., once a day or more) and then less frequently (e.g., once a week or less). The mammalian cell derived exosome containing composition or formulation can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more prior to the administration of one or more chemotherapeutic agents (e.g., prior to an event that is likely to induce pain). The mammalian cell derived exosome containing composition or formulation can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more after the administration of one or more chemotherapeutic agents or an event likely to induce pain. In other embodiments, the mammalian cell derived exosome containing composition or formulation can be administered by any discontinuous administration regimen. In one example, the mammalian cell derived exosome containing composition or formulation can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the mammalian cell derived exosome containing composition or formulation can be administered under the same or a different schedule. The period of rest can be one, two, three, or four weeks, or longer, according to the pharmacodynamic effects of the mammalian cell derived exosome containing composition or formulation on the subject.

The mammalian cell derived exosome containing composition or formulation described herein can be administered to a subject for various durations of time including about 5 minutes, 10 minutes, 30 minutes, 45 minutes, 1 hour, 2 hours, 4 hours, 6 hours, 8 hours, 12 hours, 18 hours, 24 hours or longer.

In one embodiment, the mammalian cell derived exosome containing composition or formulation of the invention can be delivered to the subject by parenteral administration. In such an embodiment, the route can be intravenous, intramuscular, subcutaneous, intranasal, intrathecal or intraarterial administration, for example, by injection or infusion. In some embodiments, therapeutically effective doses of a composition or a formulation containing mammalian cell derived exosomes, or their internal constituents thereof can be administered intravenously, or stereotactically into the spinal cord, or the dorsal root ganglion.

The composition of the invention can be delivered to the subject at a dose that is effective to treat and/or prevent pain or neurotoxicity, for example, CIPN. The effective dosage will depend on many factors including the gender, age, weight, and general physical condition of the subject, the severity of the pain, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, The Science and Practice of Pharmacy ($21^{st}$ ed. 2005)). In one embodiment, the mammalian cell derived exosome containing composition or formulation of the invention is administered at a dose of about 0.1 to about 10.0 mg/m$^2$, e.g., about 0.6 to about 4.0 mg/m$^2$, about 1.0 to about 3.0 mg/m$^2$, or about 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 mg/m$^2$. In some instances, the dose can be even lower, e.g., as low as 0.1, 0.05, 0.01, 0.005, or 0.001 mg/m$^2$ or lower. In some instances, the dose can be even higher, e.g., as high as 20, 50, 100, 500, or 1000 mg/m$^2$ or higher. The present invention encompasses every sub-range within the cited ranges and amounts.

In one embodiment, the mammalian cell derived exosome containing composition or formulation of the invention is administered at a dose of about $1\times10^1$ to about $1\times10^{15}$ mammalian cell derived exosome per kg body weight of the patient, or about $1\times10^1$ to about $1\times10^{14}$ Mammalian cell derived exosomes per kg body weight of the patient, or about $1\times10^1$ to about $1\times10^{13}$ Mammalian cell derived exosomes per kg body weight of the patient, or about $1\times10^1$ to about $1\times10^{12}$ Mammalian cell derived exosomes per kg body weight of the patient, or about $1\times10^1$ to about $1\times10^{11}$ Mammalian cell derived exosomes per kg body weight of the patient, or about $1\times10^1$ to about $1\times10^{10}$ Mammalian cell derived exosomes per kg body weight of the patient, or about $1\times10^1$ to about $1\times10^9$ Mammalian cell derived exosomes per kg body weight of the patient, or about $1\times10^1$ to about $1\times10^8$ Mammalian cell derived exosomes per kg body weight of the patient, or about $1\times10^1$ to about $1\times10^7$ Mammalian cell derived exosomes per kg body weight of the patient, or from about $1\times10^1$ to about $1\times10^6$ Mammalian cell derived exosomes per kg body weight of the patient, or from about $1\times10^1$ to about $1\times10^5$ Mammalian cell derived exosomes per kg body weight of the patient, or from about $1\times10^1$ to about $1\times10^4$ Mammalian cell derived exosomes per kg body weight of the patient, or from about $1\times10^1$ to about $1\times10^3$ Mammalian cell derived exosomes per kg body weight of the patient, or from about $1\times10^1$ to about $1\times10^2$ Mammalian cell derived exosomes per kg body weight of the patient. Preferably, the CEC derived exosome containing composition or formulation of the invention is administered at a dose of about $1\times10^9$ to about $1\times10^{15}$ Mammalian cell derived exosomes per kg body weight of the patient, or a dose of about $2.3\times10^{12}$ Mammalian cell derived exosomes for an average adult weighing approximately 70 kg. In various embodiments, the exemplified doses of Mammalian cell derived exosomes per kg weight of the patient are daily doses or therapeutically effective doses, either in unit form or in sub-unit forms to be dosed one or more times per day.

In one embodiment of the invention, the subject is one that has developed a neuropathy and the composition of the invention is administered to the subject after the development of neuropathy in order to treat the pain. In another embodiment, the subject is one that has not developed a neuropathy and the composition of the invention is administered to the subject to prevent the occurrence of pain. In one embodiment, the subject is one that is undergoing an event that is likely to result in the development of neuropathy. The composition of the invention can be delivered to the subject prior to the event occurring, concurrently with the event, and/or after the event occurs but before the development of pain. Events that are likely to result in the development of neuropathy are well known and include, without limitation, surgery (e.g., amputation, mastectomy, thoracotomy), traumatic nerve damage, radiation treatment, and chemotherapy.

In another embodiment of the invention, the subject is currently undergoing, will be undergoing, and/or has undergone chemotherapy treatment with one or more chemotherapeutic agents that are known or suspected to induce neuropathy and the Mammalian cell derived exosomes is administered to prevent and/or treat pain. Chemotherapeutic agents known to induce neuropathy include, without limitation, vinca alkaloids (e.g., vinblastine, vincristine, vindesine, vinflunine, or vinorelbine), taxanes (e.g., paclitaxel or docetaxel), platinum-based compounds (e.g., cisplatin, carboplatin, nedaplatin, triplatin tetranitrate, satraplatin, or oxaliplatin), boronic acid (bortezomib), pthaloyl derivatives (thalidomide, or lenolidamide), and epotilones (ixabepalone). Accordingly, the present invention provides a method for preventing and/or treating neurotoxicity, for example, CIPN as a result of chemotherapy treatment. In various embodiments, treatment with the following chemotherapeutic agents can include, without limitation, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfarnide, ilmofosine, interleukin II (including recombinant interleukin II or rIL2), interferon alfa-2a, interferon alfa-2b, interferon alfa-n1, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

In one embodiment of the invention, the composition of the invention is delivered to a subject concurrently with a second analgesic or drug. The second analgesic or drug can be delivered in the same composition as the CEC derived exosome containing composition or formulation or in a separate composition. The second analgesic or drug can be delivered to the subject on a different schedule or by a different route as compared to the CEC derived exosome containing composition or formulation. The second analgesic or drug can be any agent that provides a benefit to the subject. Further agents include, without limitation, chemotherapeutic agents, antiemetic agents, analgesic agents (e.g., opioids and/or systemic local anesthetics), anti-inflammatory agents, and peroxisome proliferator-activated receptor (PPAR) agonists, e.g., PPAR δ-agonists.

Treatment of Cancer Comprising Administering Therapeutically Effective Amounts of Mammalian Cell Derived Exosomes in Combination with One or More Chemotherapeutic Agents The inventors of the present invention have unexpectedly found that administration of mammalian cell derived exosomes in therapeutically effective amounts can sensitize tumor or tumor cells to the cytotoxic effects of an administered chemotherapeutic when tested against a cancer cell line, for example, when tested against cancer cell growth in vitro and xenografted tumor growth in vivo. Accordingly, the present invention provides a method to treat cancer (any form of cancer, primary cancer, primary tumors, locally advanced tumors, or metastasized tumors) in a subject in need thereof, the method comprising administering a therapeutically effective amount of a mammalian cell derived exosome containing composition or formulation in combination with one or more chemotherapeutic agents to treat the cancer in the subject.

In some embodiments, a mammalian cell derived exosome containing composition or formulation of the present invention may be formulated or administered with one or more chemotherapeutic agents as described herein for the treatment of a hyperproliferative disease, such as cancer. "Chemotherapeutic" agents include but are not limited to anti-neoplastic agents. As used herein, "anti-neoplastic agents" include both cytotoxic and cytostatic agents including biological, immunological and vaccine therapies. Combination therapies according to the invention thus comprise the administration of mammalian cell derived exosomes and at least one chemotherapeutic agent or at least one radiation therapy agent used to treat cancer.

In one embodiment, combination therapies according to the invention comprise the administration of at least one mammalian cell derived exosome containing composition or formulation of the invention, in combination with one or more chemotherapeutic agents and optionally surgical therapy. In various embodiments, the mammalian cell derived exosomes can include exosomes derived from: stem cells, mesenchymal stromal cells, umbilical cord cells, endothelial cells, (for example, cerebral endothelial cells (CEC), brain microvascular endothelial cells (BMVEC), Primary Human Brain Microvascular Endothelial Cells (PHBMVEC) (for example, ACBRI 376), endothelial progenitor cells, AG-133/CD-133+ cells and the like), Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, mastocytes, or combinations thereof. In various embodiments, the mammalian cell derived exosomes can include exosomes derived from: mesenchymal stem cells, mesenchymal stromal cells, endothelial cells and endothelial progenitor cells. In some illustrative embodiments, the mammalian cell derived exosomes are CD63+ and Alix+ exosomes. In related embodiments, the method of treating cancer in a subject in need thereof comprises, administering a therapeutically effective amount of mammalian cell derived exosomes in an amount ranging from about $1\times10^1$ to about $1\times10^{15}$ exosomes per kg body weight of the patient, or about $1\times10^9$ to about $1\times10^{15}$ exosomes per kg body weight of the patient and at least one chemotherapeutic agent. In some related embodiments, the subject is administered CEC derived exosomes at the dosages described herein.

In one embodiment, combination therapies according to the invention comprise the administration of at least one mammalian cell derived exosome containing composition or formulation of the invention and radiotherapy. In one embodiment, combination therapies according to the invention comprise the administration of at least one mammalian cell derived exosome containing composition or formulation of the invention, one or more chemotherapeutic agents, and at least one supportive care agent (e.g., at least one antiemetic agent). In one embodiment, combination therapies according to the present invention comprise the administration of at least one mammalian cell derived exosome containing composition or formulation of the invention and at least one chemotherapeutic agent. In one particular embodiment, the invention comprises the administration of at least one mammalian cell derived exosome containing composition or formulation of the invention and at least one chemotherapeutic agent e.g. an anti-neoplastic agent. In some embodiments, the combination comprises at least one CEC derived exosome containing composition or formulation of the invention and at least one chemotherapeutic agent.

When a mammalian cell derived exosome containing composition or formulation of the invention is used in combination with an anti-neoplastic or one or more chemotherapeutic agents, the dose of each active agent may differ from that when the active agent is used alone. Appropriate doses will be readily appreciated by those skilled in the art. The appropriate dose of the mammalian cell derived exosome containing composition or formulation(s) of the invention and the anti-neoplastic or one or more chemotherapeutic agents and the relative timings of administration will be selected in order to achieve the desired combined therapeutic effect, and are within the expertise and discretion of the attendant clinician.

Typically, any chemotherapeutic agent that has activity against a susceptible neoplasm being treated may be utilized in combination with the mammalian cell derived exosome containing composition or formulation of the invention, provided that the particular agent is clinically compatible with therapy employing a mammalian cell derived exosome containing composition or formulation of the invention. Typical anti-neoplastic agents useful in the present invention include, but are not limited to: alkylating agents, antimetabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the compounds of the invention in the compositions and methods described above. Examples of alkylating agents include but are not limited to nitrogen mustards such as cyclophosphamides, temozolamide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite neoplastic agents may be employed in combination with the compounds of the invention in the compositions and methods described above. Examples of antimetabolite anti-neoplastic agents include but are not limited to purine and pyrimidine analogues and anti-folate compounds, and more specifically, hydroxyurea, cytosine, arabinoside, ralitrexed, tegafur, fluorouracil (e.g., 5FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the compounds of the invention in the compositions and methods described above.

Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the compounds of the invention in the compositions and methods described above. Examples of antimitotic agents include, but are not limited to, diterpenoids, vinca alkaloids, polo-like kinase (Plk) inhibitors and CenpE inhibitors. Examples of diterpenoids include, but are not limited to, paclitaxel and its analog docetaxel. Examples of vinca alkaloids include, but are not limited to, vinblastine, vincristine, vindesine and vinorelbine. Plk inhibitors are discussed further below.

Topoisomerase inhibitors include inhibitors of Topoisomerase II and inhibitors of Topoisomerase I. Topoisomerase II inhibitors, such as epipodophyllotoxins, are anti-neoplastic agents derived from the mandrake plant, e.g., *Podophyllum* sp., that typically affect cells in the S and $G_2$ phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the CEC exosomes of the invention in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the compounds of the invention in the compositions and methods described above. Examples of hormones and hormonal analogues believed to be useful in the treatment of neoplasms include, but are not limited to antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5α-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin.

Retinoid(s) are compounds that bind to and activate at least one retinoic acid receptor selected from RARα, RARβ, and RARγ and/or compounds that bind to and activate at least one of RARα, RARβ, and RARγ and also at least one retinoic X receptor (RXR), including RXRα, RXRβ, and RXRγ. Retinoids for use in the present invention typically have affinity for RAR, and particularly for RARα and/or RARβ. However, certain synthetic retinoids, such as 9-cis-retinoic acid also have affinity for both RAR and RXR. In one embodiment, the retinoid has affinity for RARα (and RARα agonist).

Signal transduction pathway inhibitors are those inhibitors which block or inhibit a chemical process which evokes an intracellular change. As used herein these changes include, but are not limited to, cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor tyrosine kinase inhibitors which may be combined with the compounds of the invention include those involved in the regulation of cell growth, which receptor tyrosine kinases are sometimes referred to as "growth factor receptors." Examples of growth factor receptor inhibitors, include but are not limited to inhibitors of: insulin growth factor receptors (IGF-1R, IR and IRR); epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-fms), c-kit, c-met, fibroblast growth factor receptors (FGFRs), hepatocyte growth factor receptors (HGFRs), Trk receptors (TrkA, TrkB, and TrkC), ephrin (Eph) receptors and the RET protooncogene.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib (GLEEVEC®) is one example of a PDGFR inhibitor. Examples of VEGFR inhibitors include pazopanib, ZD6474, AZD2171, PTK787, sunitinib and sorafenib.

In one embodiment, the invention provides methods of treatment of any of the various cancers enumerated above comprising administering a mammalian cell derived exosome, for example, a mammalian cell derived exosome containing composition or formulation in combination with an EGFR or ErbB inhibitor. In one particular embodiment, the methods of the present invention comprise administering a mammalian cell derived exosome containing composition or formulation of the invention in combination with lapatinib. In one particular embodiment, the methods of the present invention comprise administering a mammalian cell derived exosome containing composition or formulation of the invention in combination with trastuzumab. In one particular embodiment, the methods of the present invention comprise administering a mammalian cell derived exosome containing composition or formulation of the invention in combination with erlotinib. In one particular embodiment, the methods of the present invention comprise administering a mammalian cell derived exosome containing composition or formulation of the invention in combination with gefitinib.

In another embodiment, the present invention provides methods of treatment of any of the various conditions enumerated above comprising administering a mammalian cell derived exosome containing composition or formulation of the invention in combination with a VEGFR inhibitor. In one particular embodiment, the methods of the present invention comprise administering a CEC derived exosome containing composition or formulation of the invention in combination with pazopanib.

In each of the aforementioned methods of treatment using the illustrated inhibitors, the mammalian cell derived exosomes are CEC derived exosomes.

Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, Abl kinase (c-Abl and Bcr-Abl), FAK (focal adhesion kinase) and Bruton's tyrosine kinase (BTK). Non-receptor kinases and agents, which inhibit non-receptor tyrosine kinase function, are described in Sinha, S, and Corey, S. J., (1999) J. Hemather. Stem Cell Res. 8:465-80; and Bolen, J. B. and Brugge, J. S., (1997) Annu. Rev. of Immunol. 15:371-404.

SH2/SH3 domain blockers are agents that disrupt SH2 or SH3 domain binding in a variety of enzymes or adaptor proteins including, but not limited to, PI3-K p85 subunit, Src family kinases, adaptor molecules (Shc, Crk, Nck, Grb2) and Ras-GAP. Examples of Src inhibitors include, but are not limited to, dasatinib and BMS-354825 (J. Med. Chem. (2004) 47:6658-6661).

Inhibitors of serine/threonine kinases may also be used in combination with the CEC derived exosome containing composition or formulations of the invention in any of the compositions and methods described above. Examples of serine/threonine kinase inhibitors that may also be used in combination with a CEC derived exosome containing composition or formulation of the present invention include, but are not limited to, polo-like kinase inhibitors (Plk family e.g., Plk1, Plk2, and Plk3), which play critical roles in regulating processes in the cell cycle including the entry into and the exit from mitosis; MAP kinase cascade blockers, which include other Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers, including inhibitors of PKC subtypes (alpha, beta, gamma, epsilon, mu, lambda, iota, zeta); inhibitors of kappa-B (IkB) kinase family (IKK-alpha, IKK-beta); PKB/Akt kinase family inhibitors; and inhibitors of TGF-beta receptor kinases. Other examples of serine/threonine kinase inhibitors are known in the art. In another embodiment, the present invention provides methods of treatment of any of the various conditions enumerated above comprising administering a CEC derived exosome containing composition or formulation of the invention in combination with a Plk inhibitor.

Urokinase, also referred to as urokinase-type Plasminogen Activator (uPA), is a serine protease. Activation of the serine protease plasmin triggers a proteolysis cascade which is involved in thrombolysis or extracellular matrix degradation. Elevated expression of urokinase and several other components of the plasminogen activation system have been correlated with tumor malignancy including several aspects of cancer biology such as cell adhesion, migration and cellular mitotic pathways as well. Inhibitors of urokinase expression may be used in combination with the CEC derived exosome containing composition or formulations of the invention in the compositions and methods described above.

Inhibitors of Ras oncogene may also be useful in combination with the CEC derived exosome containing composition or formulations of the present invention. Such inhibitors include, but are not limited to, inhibitors of farnesyltransferase, geranyl-geranyl transferase, and CAAX proteases as well as anti-sense oligonucleotides, ribozymes and immunotherapy. Such inhibitors have been shown to block Ras activation in cells containing mutant Ras, thereby acting as antiproliferative agents.

Inhibitors of kinases involved in the IGF-1R signaling axis may also be useful in combination with the CEC derived exosome containing composition or formulations of the present invention. Such inhibitors include but are not limited to inhibitors of JNK1/2/3, PI3K, AKT and MEK, and 14.3.3 signaling inhibitors.

Cell cycle signaling inhibitors, including inhibitors of cyclin dependent kinases (CDKs) are also useful in combination with the CEC derived exosome containing composition or formulations of the invention in the compositions and methods described above. Examples of cyclin dependent kinases, including CDK2, CDK4, and CDK6 and inhibitors for the same are described in, for instance, Rosania G. R., et al., Exp. Opin. Ther. Patents (2000) 10:215-230.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the CEC derived exosome containing composition or formulations of the invention. For example, anti-VEGF antibodies, which do not recognize VEGFR (the receptor tyrosine kinase), but bind to the ligand; small molecule inhibitors of integrin (alpha$_v$, beta$_3$) that inhibit angiogenesis; endostatin and angiostatin (non-RTK) may also prove useful in combination with the CEC derived exosome containing composition or formulations of the invention. One example of a VEGFR antibody is bevacizumab (AVASTIN®). Inhibitors of phosphatidyl inositol-3-OH kinase family members including blockers of PI3-kinase, ATM, DNA-PK, and Ku may also be useful in combination with the present invention.

In some embodiments, CEC derived exosome containing composition or formulations of the present invention may be administered before, concomitantly or after the administration of the following exemplary chemotherapeutics: inhibitors of topoisomerase I and II activity, such as camptothecin, drugs such as irinotecan, topotecan and rubitecan, alkylating agents such as temozolomide and DTIC (dacarbazine), and platinum agents like oxaliplatin, cisplatin, cisplatin-doxorubicin-cyclophosphamide, carboplatin, and carboplatin-paclitaxel, doxorubicin, doxorubicin-cyclophosphamide, capecitabine, cyclophosphamide-methotrexate-5-fluorouracil, docetaxel, paclitaxel, 5-fluoracil-epirubicin-cyclophosphamide, paclitaxel, vinorelbine, etoposide, pegylated liposomal doxorubicin and topotecan. In some embodiments, the chemotherapeutic useful to be used in combination with the exosome compositions of the present invention, may include: Platinum agents: cisplatin, carboplatin, oxaliplatin, Vinca alkaloids: vincristine, vinblastine, Taxanes: paclitaxel, docetaxel, Epothilones: ixabepalone, and bortezomib, thalidomide, and lenolidamide.

The present invention has identified several unexpected findings as illustrated in the examples section below. One such unexpected finding includes the discovery that when cancer cells are contacted with mammalian cell derived exosomes, for example, CEC derived exosomes, and a chemotherapeutic agent, the cancer cells become sensitized to the effects of the administered chemotherapeutic agent. The present invention therefor enables the chemotherapeutic agent to be administered or used in a dosage regimen at a concentration that is lower than the standard therapeutic dosage for administering the chemotherapeutic agent to a similar subject having the same or similar cancer. Alternatively, the present invention therefor enables the chemotherapeutic agent to be administered or used in a dosage regimen at a concentration that is higher than the standard therapeutic dosage for administering the chemotherapeutic agent to a similar subject having the same or similar cancer.

Those of ordinary skill in the art understands and administers chemotherapeutic agents based on the directions of a regulatory agency and the directions provided on the label associated with each approved chemotherapeutic agent. Accordingly, the combination comprising a mammalian cell derived exosome containing composition (for example, CEC-derived exosomes), and one or more chemotherapeutic agents permits dosing the chemotherapeutic agent(s) of the combination at sub-therapeutic doses or at higher doses than the doses which are approved for use in a specific cancer patient population. Since the dose of the chemotherapeutic agent in the combination is administered at a lower or higher concentration or amount than the dose approved for use in a specific cancer population based on a similar weight, age, type and stage of cancer, (i.e. a maximally tolerated dose, optionally titrated to avoid unwanted side effects individually catered for the specific patient) then the subject is expected to tolerate the chemotherapeutic agent used in the combination for a longer period compared to the dose of the chemotherapeutic agent when dosed alone. As used herein, approved doses of chemotherapeutic doses are doses that are approved by a regulatory agency for use by a specific patient population for a specific cancer treatment, which is typically recited in the label accompanying each approved chemotherapeutic agent for use in their respective cancer treatment.

Another unexpected finding is that since the combination comprising a mammalian cell derived exosome containing composition (for example, CEC-derived exosomes) sensitizes the tumor or cancer cells to the effects of the chemotherapeutic agent, then the administration of the combination permits a lower dosage of the chemotherapeutic agent which may then reduce, ameliorate or eliminate one or more side effects (for example, neurotoxicity) associated with multiple administrations of the chemotherapeutic agent when used alone in a population of similar subjects treated for the same or similar cancer.

Another unexpected finding is that since the combination comprising a mammalian cell derived exosome containing composition (for example, CEC-derived exosomes) sensitizes the tumor or cancer cells to the effects of the chemotherapeutic agent, then the administration of the combination permits a higher dosage of the chemotherapeutic agent which may then reduce, ameliorate or eliminate one or more side effects (for example, neurotoxicity) associated with multiple administrations of the chemotherapeutic agent when used alone in a population of similar subjects treated for the same or similar cancer.

While some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. It is intended that the following claims define the scope of the invention and that the methods, systems, and compositions within the scope of these claims and their equivalents be covered thereby. This description of some embodiments should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

Examples

The following examples are provided without limiting embodiments to only those embodiments described below and without waiving or disclaiming any embodiments or subject matter.

The present inventors have unexpectedly found that oxaliplatin dose-dependently inhibited the axonal growth of DRG neurons in a cell body independent manner. However, exosomes derived from cerebral endothelial cells (CECs) referred to herein as CEC-exosomes, completely reversed the inhibitory effect of oxaliplatin on axonal growth of DRG neurons. Moreover, CEC-exosomes when used alone did not affect the growth of tumor cells (human colon carcinoma HCT-116 and human ovarian carcinoma OVCAR3). However, in the presence of oxaliplatin, CEC-exosomes enhanced the cytotoxicity of oxaliplatin when administered to tumor cells. The data presented in the examples section herein, demonstrates that CEC-exosomes are effective to mitigate peripheral neurotoxicity induced by chemotherapeutic agents as disclosed herein, for example, platinum-based chemotherapy, and that CEC-exosomes can enhance the efficacy of a cancer therapeutic, for example, a platinum-based chemotherapy on tumor cells. Thus, the inventors have discovered that CEC-exosomes can reduce the chemotherapy-induced neurotoxicity including peripheral neuropathy in cancer patients, and are able to sensitize tumor cells to chemotherapy.

Inhibiting the Neurotoxic Effects of Chemotherapeutic Treatment

While the present invention was exemplified with platinum based chemotherapeutic agents, the present methods for inhibiting neurotoxicity and CIPN are not so limited to treating CIPN caused by platinum based chemotherapeutic agents, but many different classes of anticancer, anti-neoplastic, or chemotherapeutic agents as described herein. Platinum-based anticancer agents are commonly used to treat lung, colorectal, ovarian, breast, head/neck, and genitourinary cancers. However, the platinum agents have the propensity to enter the dorsal root ganglion (DRG) and peripheral nerves compared to the brain. They cannot pass the blood-brain barrier and accumulate in the DRG neurons. Platinum agent-induced peripheral neurotoxicity is a common adverse side-effect that interferes the anticancer therapy. Unfortunately, no strategy has been established to precisely balance the effectiveness and neurotoxicity. Exosomes are nano-sized extracellular vesicles secreted from diverse cells and play a role in the cell-cell communication by delivering their cargo, biomaterials, to recipient cells. The use of exosomes as a bioavailable vehicle to transport anti-tumor compounds or cell-derived biomaterial has attracted attention in cancer therapy. Exosomes released by tumor cells may act as biomarkers to identify the cancers and promote the invasion, metastasis and tumor growths. In addition, exosomes may act as a tumor vaccine to suppress T-cell modulated immunologic cytotoxicity. Surprisingly, we found for the first time, that the exosomes derived from cerebral endothelial cells enhance the toxicity of chemotherapeutic agents to tumors, and thereby provide a means to augment chemotherapy.

Endothelial cells (ECs), major cellular components of blood vessels, are commonly known as supporters of the different stages of the neoplastic process. Angiogenic vessels provide the supply of nutrients by abundantly generated ECs. On the other hand, in the nervous system, angiogenesis couples with neurogenesis during cerebral ischemia. The highly branched and hierarchical blood vessels formed by CECs, play pivotal roles in neuronal remodeling. In the nervous system, the branching of axons is patterned with vasculature. In addition, the specialized ECs at the distal ends of endothelial cells sprout during angiogenesis and have the similar growth feature like axonal growth cone. Endothelial and axonal sprouting share the same groups of neuronal guidance factors, thus, a close supporting relationship exists between cerebral endothelial cells and axons. Emerging data show that exosomes modulate the interaction of axons and glia, such as oligodendrocyte-neuron communication in the brain's. In addition, exosomes released from Schwann cells were found to promote axonal growth of DRG neurons.

We first examined whether platinum compounds directly affect distal axon growth of DRG neurons. Oxaliplatin, a third generation platinum compound, was selected based on the fact that it is routinely used for the treatment of colorectal cancer, and other cancers. Primary rat DRG neurons were cultured in a microfluidic device that separates distal axons within the axonal compartment from their parent cell bodies within the cell body compartment as shown in FIG. 1 panel A. During 24 h culture, the neurons extended their axons to pass through a 450 nm long microgrooves, leading to only distal axons to grow into the axonal compartment (FIG. 1A). Oxaliplatin at various doses was applied into the axonal compartment (FIG. 1B). We found that oxaliplatin dose-dependently (Half Maximal Inhibitory Concentration, $IC_{50}$=9.1 nM) inhibited the growth of axons (see FIG. 1C). These data indicate that oxaliplatin can directly act on axons to block axonal growth, which may contribute to peripheral neuropathy.

We then investigated whether CEC derived exosomes can affect the inhibitory effect of oxaliplatin on axonal growth. CEC derived exosomes were isolated from cultured primary CECs harvested from adult rats according to our published protocols (Teng et al, JCBFM, 2008, 28; 764-771, for culturing endothelial cells, Xin et al, Stem Cells, 2012, 30; 1556-1564 for isolation of exosomes, the disclosure of which is hereby incorporated by reference in its entirety). Briefly, exosome isolation procedures were performed at 4° C. as described in the literature: Khatua A K, Taylor H E, Hildreth J E, et al. Exosomes packaging APO-BEC3G confer human immunodeficiency virus resistance to recipient cells. J Virol. 2009; 83:512-521. [PubMed:18987139]; and Wang S, Cesca F, Loers G, et al. Synapsin I is an oligomannose-carrying glycoprotein, acts as an oligomannose-binding lectin, and promotes neurite outgrowth and neuronal survival when released via glia-derived exosomes. J Neurosci. 2011; 31:7275-7290. [PubMed: 21593312].

Figure 2:
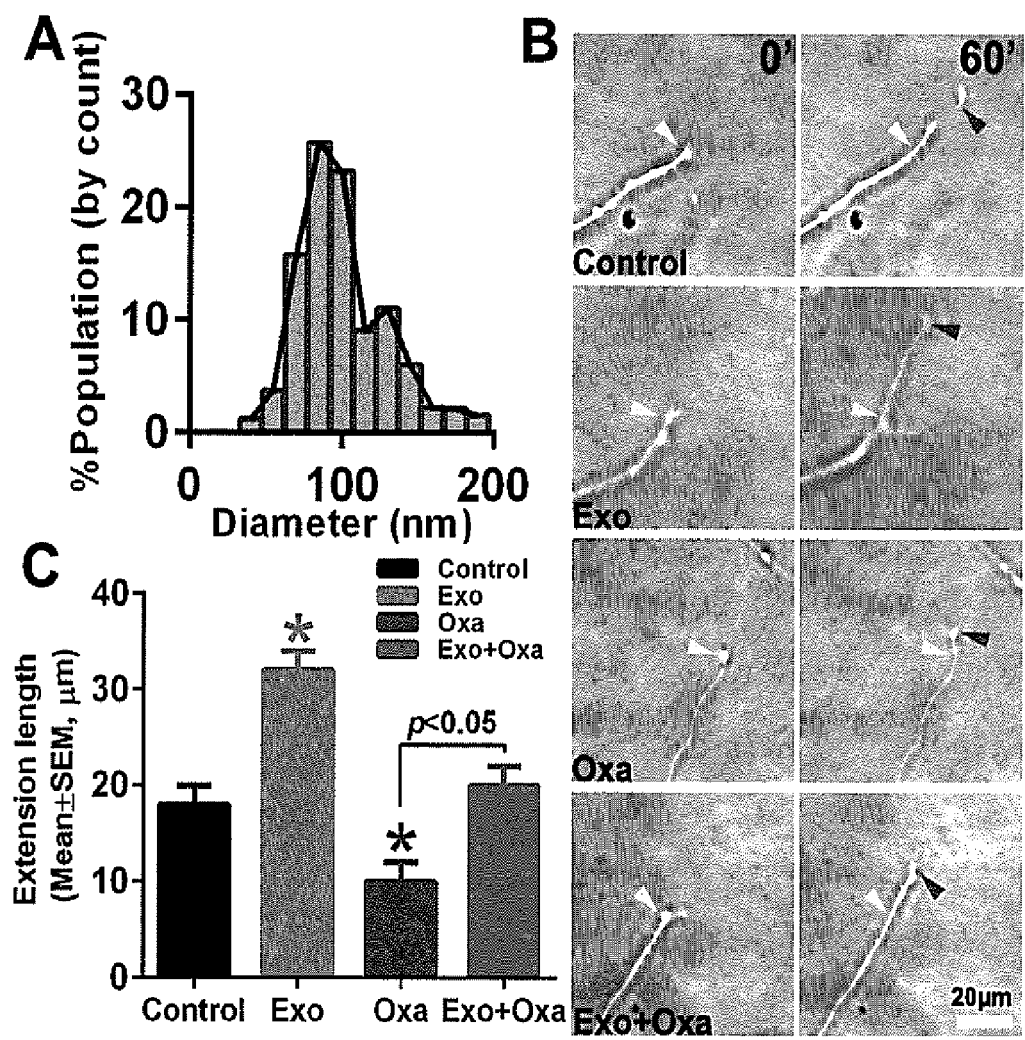
FIG. 2A is data representation showing isolation of cerebral endothelial cell (CEC) derived exosomes and the effect of CEC derived exosomes on axonal growth in the presence of oxaliplatin showing a population distribution of CEC-exosomes with different diameters measured by a qNano® system.
FIG. 2B depict photomicrographs representing time-lapse images (B) show the extension length of axon growth cone of DRG neurons in groups of control, CEC-exosome treatment ($3\times10^7$ exosomes), Oxaliplatin treatment (9.1 nM, Oxa) and CEC-exosomes combined with Oxaliplatin treatment (Exo+Oxa). Arrows in FIG. 2B indicate a growth cone at time 0 and time 60 minutes as indicated, respectively.
FIG. 2C is a bar graph representing the quantitative data extension length of axon growth cone of DRG neurons in groups of control, CEC-exosome treatment (3×107 exosomes), Oxaliplatin treatment (9.1 nM, Oxa) and CEC-exosomes combined with Oxaliplatin treatment (Exo+Oxa). * $p<0.05$ vs control, n=3/group.

Briefly, CECs were isolated from normal adult rats (n=4 per isolation). The cerebella, white matter, meninges were removed under a microscope. The cerebral cortex and subcortex of the brain were cut into small pieces in a RPMI1640, and rinsed twice to remove the blood. The tissues were homogenized with a loose fitting homogenizer for 2-3 strokes. The homogenates were then resuspended in 15% dextran (Sigma-Aldrich, 00893) and centrifuged at 10,000 g for 15 min to collect the pellet. The 0.1% collagenase/dispase with 2% FBS was used to digest the pellet for 6~8 hours and then sent to a centrifugation in a colloidal silica gradient solution of 45% Percoll at 20,000 g for 20 min. The uppermost band with single cells and fragments of microvessels were carefully collected. The CEC culture was initialed on a Collagen I (BD Biosciences, Bedford, Mass., USA) coated plates. Cultures were maintained in endothelial growth medium. The Passage 1 to 2 endothelial cells were employed to collect medium for isolation of exosomes. The growth medium of cultured CECs was collected after 48~72 h culture according to the time reach to 80% confluent. A 0.22 μm filter (Millipore, Calif.) was used to filter out dead cell and large debris. A 10,000 g for 30 minutes was performed to further remove small debris. A 100,000 g centrifugation for 3 hours was then performed to collect the exosomes. The pellet was diluted by sterilized PBS. The supernatant at this secondary centrifuge was also collected as the negative control. The particle numbers and size of harvested CEC-exosomes were calculated and analyzed by qNano system (IZON, UK) (see FIG. 2, panel A). Transmission electron microscopy (TEM) and Western blot analysis were performed to characterize CEC-exosomes before the application of exosomes for the treatment. Total proteins from CEC-exosomes were collected using 2× lysis buffer (RIPA, sigma) to lyse exosome samples. The following primary antibodies were used to detect the presence of exosomal markers (Alix and CD63) and the endothelial protein CD31: mouse monoclonal anti-Alix (1:500; Cell Signaling), rabbit polyclonal anti-CD63 (1:500; sc-15363, Santa Cruz), rabbit polyclonal anti-CD31 (1:500, MAB1393, Anti-PECAM-1, EMD Millipore).

CEC derived exosomes ($3 \times 10^7$ exosomes) were placed into the axonal compartment of the microfluidic chamber for 24 h and found that CEC-exosomes significantly promoted axonal growth measured by the time-lapse microscopy ($32 \pm 2$ μm/h vs $18 \pm 2$ μm/h in control group, n=30, p<0.01), indicating that CEC-exosomes enhance axonal growth (see FIG. 2A-2C). Moreover, when CEC-exosomes were applied into the axonal compartment in the presence of oxaliplatin (at the dose of $IC_{50}$ 9.1 nM), they completely blocked oxaliplatin-induced inhibitory effect on distal axonal growth as shown in FIGS. 2B and 2C), suggesting that the CEC derived exosomes mitigate neurotoxicity induced by oxaliplatin.

To investigate the effect of CEC-exosomes on tumor cells, human colon carcinoma HCT-116 and human ovarian carcinoma OVCAR3 were incubated with CEC derived exosomes ($3 \times 10^2$ exosomes) and inhibitory concentrations of oxaliplatin. Tumor cell viability was measured using an MTT assay. The experimental results obtained indicate that CEC derived exosomes enhanced the cytotoxicity of oxaliplatin against HCT-116 ($IC_{50}$ reduced from $16.1 \pm 2.1$ μM to $6.9 \pm 1.0$ μM, reverse folds (IRF)=$2.3 \pm 0.1$, n=3, p<0.05) and OVCAR3 ($IC_{50}$ reduced from $6.5 \pm 1.1$ μM to $2.3 \pm 0.1$ μM, IRF=$2.8 \pm 0.2$, n=3, p<0.05). These data indicate that CEC derived exosomes when administered prior to or concurrently with oxaliplatin sensitizes tumor cells to oxaliplatin.

The reduced concentrations of oxaliplatin which when administered with CEC derived exosomes were found to be effective in inhibiting cancer cell lines: human colon carcinoma HCT-116 and human ovarian carcinoma OVCAR3. Such lowered concentrations of oxaliplatin although cytotoxic against the tumor cell lines, also had the added benefit of reducing the inhibition of axonal growth of DRG neurons. For example, when DRG neurons were incubated with a reduced concentration of oxaliplatin (3.6 nM) with an IRF of 2.5, the axonal growth was inhibited by 27%, whereas a regular dose of oxaliplatin (9.1 nM) used in the earlier experiments suppressed axonal growth by 50%.

Figure 3:
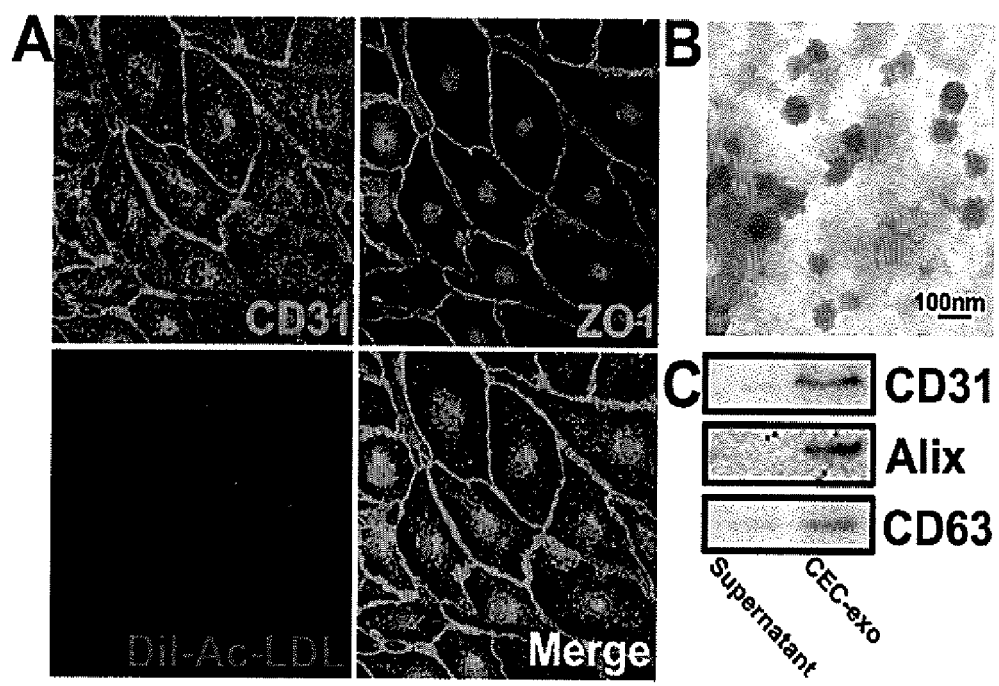
FIG. 3A depict photomicrographs illustrating cerebral endothelial cell morphology and exosomes isolated from cerebral endothelial cells. The cultured cerebral endothelial cells exhibit endothelial phenotype markers, CD31 and tight junction protein of ZO1 and also LDL positive.
FIG. 3B depicts a TEM image showing that isolated particles from supernatant of cultured CECs are approximately 125 nm.
FIG. 3C depicts a Western blot analysis of harvested exosomes shows that the exosomes contain endothelial cell protein CD31 and exosome marker protein Alix and CD63.

In another experiment, CECs isolated from healthy young adult rat brain were characterized by showing that the cultured CECs exhibit endothelial phenotype markers, CD31 and tight junction protein of ZO1 and also LDL positive, another marker of endothelial cells (See FIG. 3A). After that, using TEM and Western blot, we examined isolated particles (exosomes) from supernatants of cultured CECs. TEM analysis revealed these particles have approximately 125 nm ultrastructures, while Western blot analysis showed that these nanoparticles contain exosomal biomarker proteins Alix and CD63 as well as endothelial marker protein, CD31 as shown in FIGS. 3B &3C. Thus, these data strongly indicate that CEC-derived exosomes were isolated.

In another experiment, Female c57/b mice at age of 4 to 6 weeks were treated with Oxaliplatin at a dose of 3.5 mg/kg (i.v.) biweekly for 4 weeks. After that, mice were treated with Oxaliplatin and CEC-exosomes ($3 \times 10^{11}$ exosomes/mouse), or lysed exosomes. Mice treated with CEC-exosomes or lysed exosomes alone were used as control groups. Mechanical and thermal sensitivities as well as nerve conduction velocity were examined 2 weeks after CEC-exosome treatment. Below are the results.

TABLE 1

The effect of oxaliplatin and CEC-exosomes on Tactile allodynia (Von Frey Hairs Test)

| Groups | Before treatment | | 2 weeks after CEC-exosome treatment | |
|---|---|---|---|---|
| | 50% g threshold | P-value | 50% g threshold | P-value |
| CEC-exosomes + Oxaliplatin | 0.79 ± 0.14 | 0.48292 | 1.28 ± 0.19 | 0.048292* |
| Lysed exosomes + Oxaliplatin | 0.65 ± 0.12 | | 0.79 ± 0.09 | |
| CEC-exosomes | 1.29 ± 0.38 | 0.667222 | 1.66 ± 0.53 | 0.597999 |
| Lysed exosomes | 1.60 ± 0.58 | | 1.31 ± 0.37 | |

*Statistically significant (p ≤ 0.05)

TABLE 2

The effect of oxaliplatin and CEC-exosomes on Heat allodynia

| Groups | Before treatment | | 2 weeks after CEC-exosome treatment | |
|---|---|---|---|---|
| | paw withdraw time (s) | P-value | paw withdraw time (s) | P-value |
| CEC-exosomes + Oxaliplatin | 9.77 ± 2.32 | 0.79 | 17.26 ± 1.04 | 0.0043* |
| Lysed exosomes + Oxaliplatin | 9.11 ± 0.72 | | 9.51 ± 1.38 | |
| CEC-exosomes | 21.18 ± 1.82 | 0.18 | 16.40 ± 2.30 | 0.41 |
| Lysed exosomes | 17.73 ± 1.53 | | 20.20 ± 3.74 | |

*Statistically significant (p ≤ 0.05)

TABLE 3

The effect of oxaliplatin and CEC-exosomes on sciatic sensory nerve conduction velocity (SCV)

| Groups | Before treatment | | 2 weeks after CEC-exosome treatment | |
|---|---|---|---|---|
| | SCV (m/s) | P-value | SCV (m/s) | P-value |
| CEC-exosomes + Oxaliplatin | 17.2 ± 2.0 | 0.69 | 28.5 ± 3.4 | 0.05 |
| Lysed exosomes + Oxaliplatin | 17.0 ± 1.2 | | 19.4 ± 3.2 | |
| CEC-exosomes | 26.1 ± 3.3 | 0.48 | 25.1 ± 1.8 | 0.82 |
| Lysed exosomes | 30.8 ± 4.4 | | 24.1 ± 3.1 | |

*Statistically significant (p ≤ 0.05)

To non-invasively monitor ovarian tumor growth in vivo, female Nu/Nu mice were subcutaneously xenografted with human ovarian cells, SKOV-3/Luc cells (Cellbiolabs, AKR-232), into the dorsum. The SKOV-3/Luc cell line stably express firefly luciferase gene that emits photons which can be non-invasively imaged with IVIS spectrum system. After 3~4 week's growth, the tumor tissue was removed from the dorsum of nude mice. The envelope and inner necrosis sections of tumor were carefully removed. Tumor tissues were then chopped into $3 \times 3 \times 3$ mm³ pieces followed with 2 times rinse by PBS and then be implanted subcutaneously at the dorsum using a trocar with one piece per mice.

Development of tumor in tumor bearing nude mice was imaged with IVIS spectrum system after injection of luciferin (i.p.). Briefly, tumor bearing nude mice were anesthetized and luciferin at 100 mg/kg was administered 9 minutes prior to imaging. Six consecutive recording sequences with different binning and exposure times were used to determine the time when peak of the total counts of luciferase Flux occurs (12 min in this study). The measurement Flux was performed every week for a total of 8 consecutive weeks starting 1 week after tumor tissue implantation designated as week 0. The week 0 data were used as the baseline and data acquired from week 1 to week 7 were normalized to week 0 data. The data are presented as growth fold changes.

Figure 4:
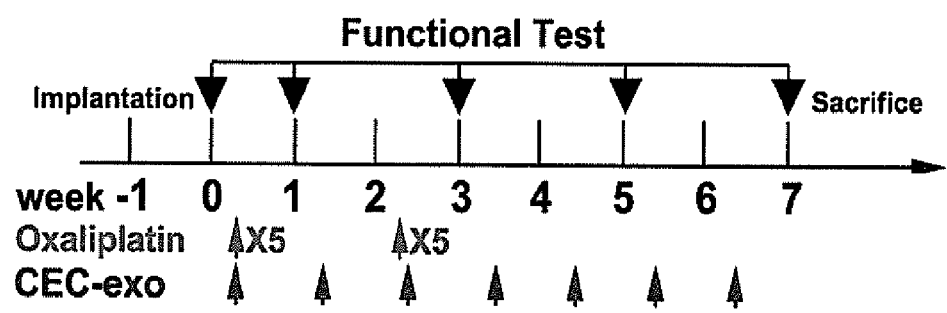
FIG. 4 depicts a protocol timeline of four experimental mice groups 1) lysed CEC-exosomes; 2) CEC-exosomes; 3) oxaliplatin; 4) oxaliplatin plus CEC-exosomes. CEC-exosomes were administered ($3\times10^{11}$ particles/mouse, i.v.) every other day at 3 times per week for 6 consecutive weeks starting from week 1 to week 6 as described in the Example section.

There were four experimental groups: 1) lysed CEC-exosomes; 2) CEC-exosomes; 3) oxaliplatin; 4) oxaliplatin plus CEC-exosomes. CEC-exosomes were administered ($3 \times 10^{11}$ particles/mouse, i.v.) every other day at 3 times per week for 6 consecutive weeks starting from week 1 to week 6 (See FIG. 4). Oxaliplatin was administered (3.0 mg/kg, i.p.) daily for two rounds of 5 consecutive days per week at week 1 and week 3, with one week interval between the treatments (FIG. 4). Measurements of tactile (Von Frey test) and cold allodynia (cold plate test), and neurophysiology were performed to examine peripheral neuropathy at week 0, week 1, week 3, week 5 and week 7 (Functional test, FIG. 4). All animals were sacrificed at week 7 after the last measurements were done. Tumor tissue, tissues of DRG, sciatic nerve, and footpad were collected for further analysis.

Figure 5:
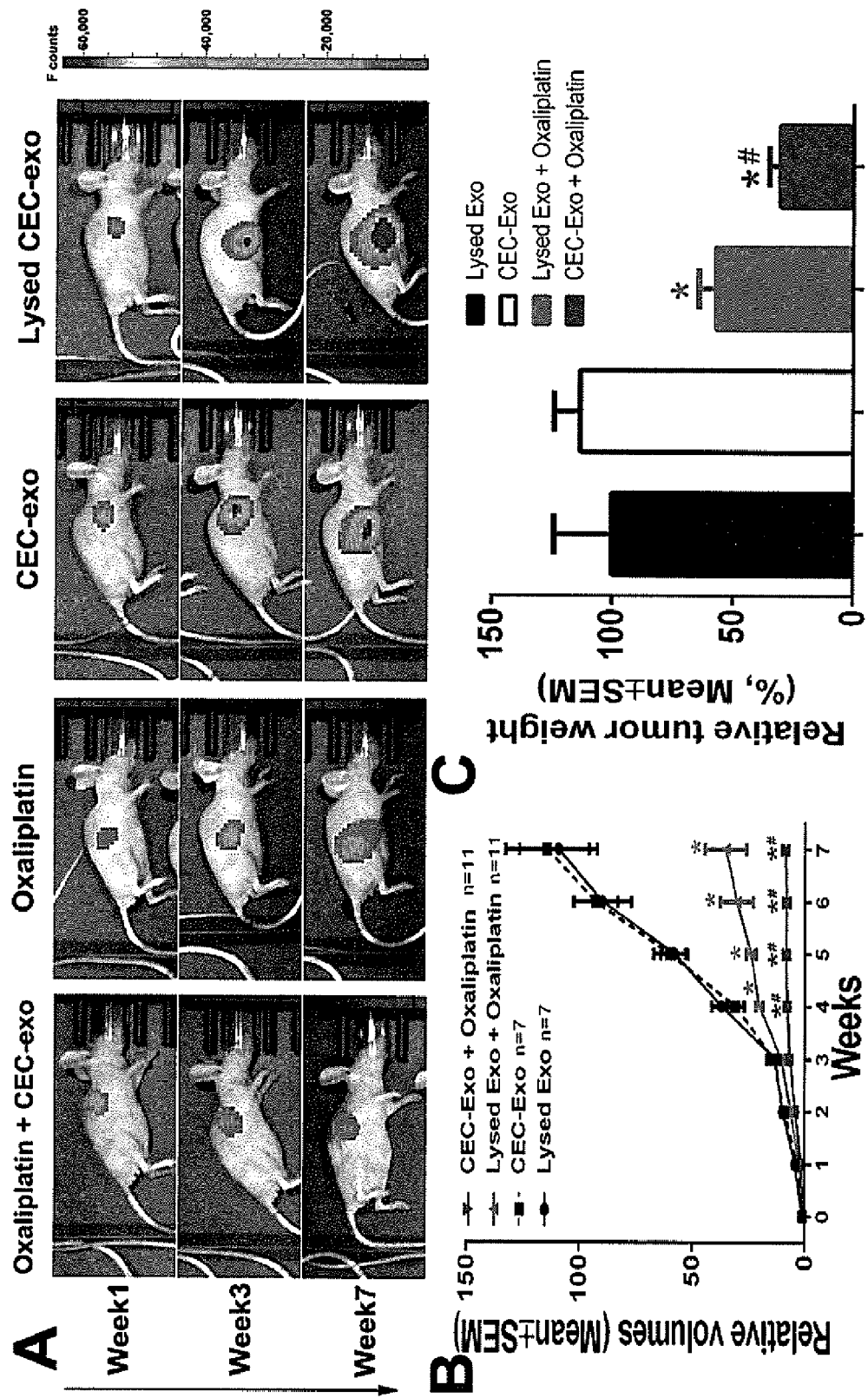
FIG. 5A depicts photographs of treated mice showing the growth of tumors after experimental treatments.
FIG. 5B is a line graph depicting the quantitative data of the animals shown in FIG. 5A, specifically tumor growth measured in relative tumor volume units.
FIG. 5C depicts a bar graph depicting the quantitative data of the animals shown in FIG. 5A, specifically tumor growth measured in relative tumor weight units.

The tumor bearing mice treated with oxaliplatin and lysed CEC-exosomes significantly reduced tumor growth by ~50% measured by luciferase signals and tumor weight, whereas oxaliplatin in combination with CEC-exosomes further significantly decreased tumor size by ~80% (FIGS. 5A-5C). These results demonstrated that CEC-exosomes significantly increase the antitumor effects of oxaliplatin on the tumor growth.

Figure 6:
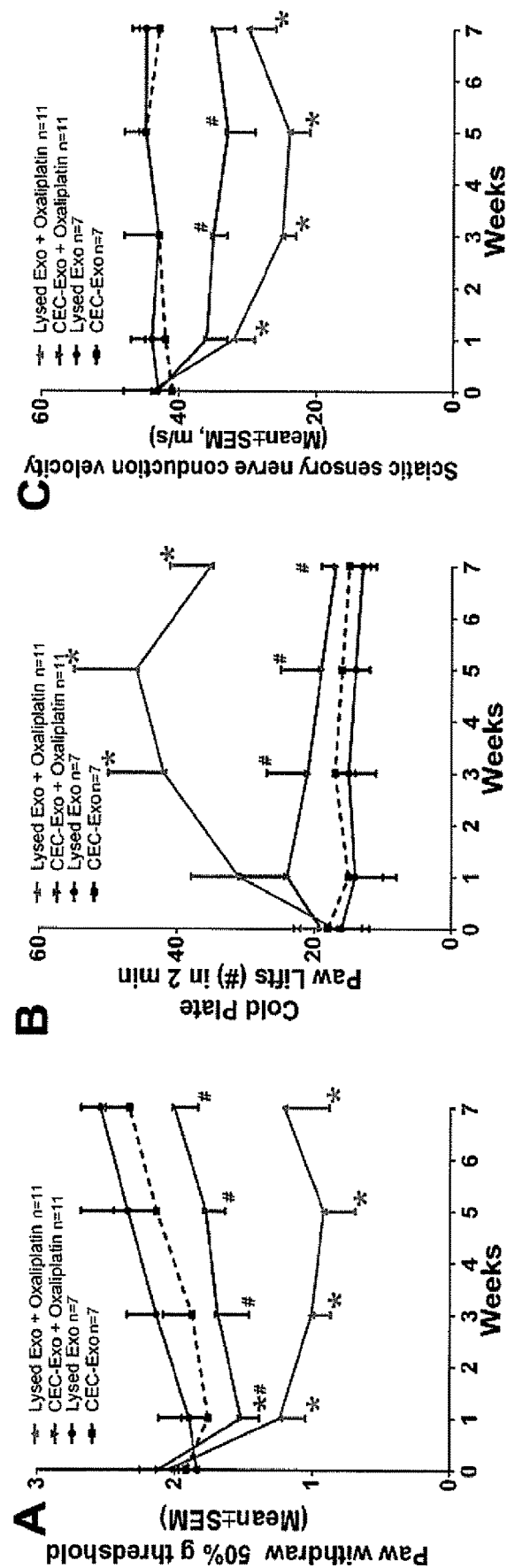
FIG. 6A depicts a line graph measuring the peripheral neuropathy measured by tactile and cold allodynia, and reduction of sensory nerve conduction velocity measured as a function of paw withdrawal compared to the control mice under the four experimental treatments described in FIG. 4.
FIG. 6B depicts a line graph measuring the peripheral neuropathy measured by tactile and cold allodynia, and reduction of sensory nerve conduction velocity measured as a function of cold allodynia compared to the control mice under the four experimental treatments described in FIG. 4.
FIG. 6C depicts a line graph measuring the peripheral neuropathy measured by tactile and cold allodynia, and reduction of sensory nerve conduction velocity measured as a function of reduction of sensory nerve conduction velocity compared to the control mice under the four experimental treatments described in FIG. 4.

The tumor bearing mice treated with oxaliplatin and lysed CEC-exos exhibited marked peripheral neuropathy measured by tactile and cold allodynia, and reduction of sensory nerve conduction velocity compared to the control mice (FIG. 6A-6C). However, the treatment with oxaliplatin and CEC-exosomes significantly reduced oxaliplatin-induced peripheral neuropathy (FIG. 6A-6C). These data demonstrated that CEC-exosomes mitigate oxaliplatin-induced peripheral neuropathy.

Figure 7:
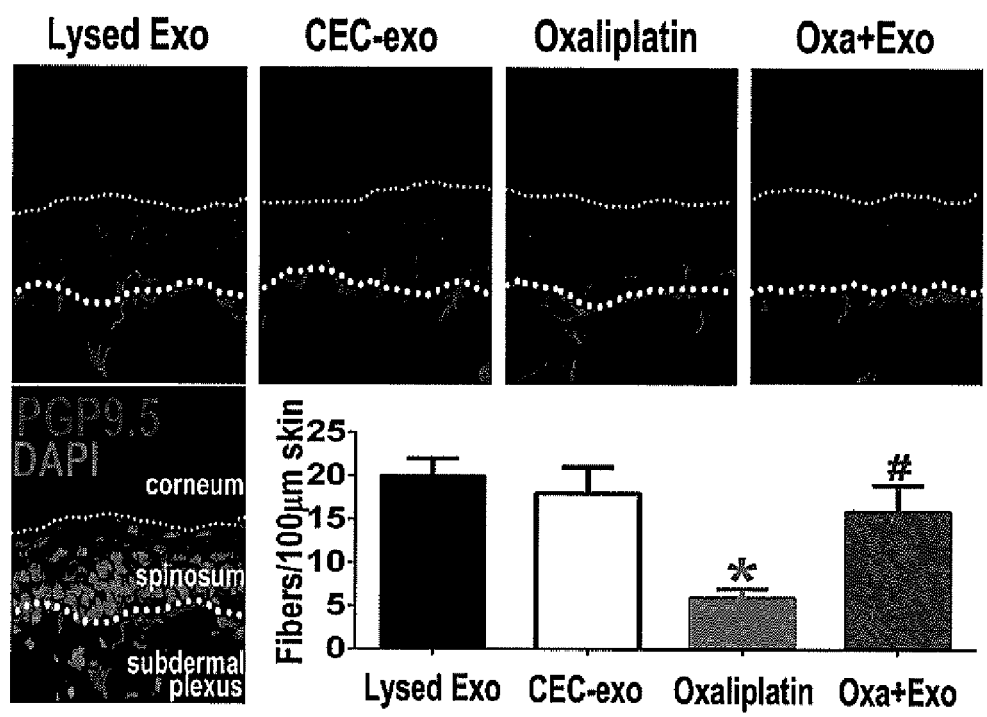
FIG. 7 depicts photomicrographs illustrating reduced intraepidermal nerve fiber (IEFN) density and a bar graph depicting the number of PGP9.5 positive fibers in response to the four treatments described in FIG. 4.
Figure 8:
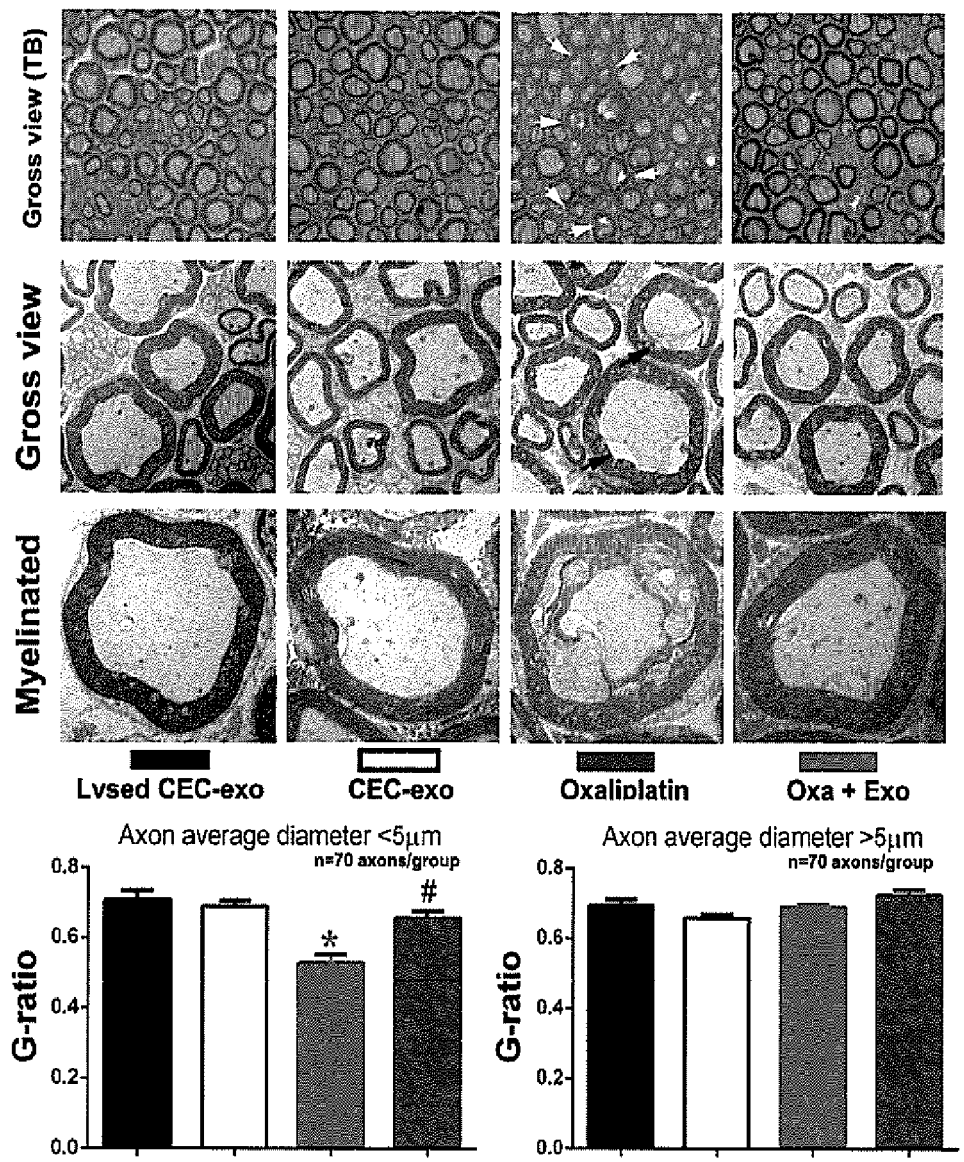
FIG. 8 depicts transmission electron microscopy (TEM) micrographs of small fibers and the extent axonal degeneration/demyelination in the small fibers (axon diameter <5 μm) in response to the four treatments described in FIG. 4, and the quantitative data represented in the bar graphs.
Figure 9:
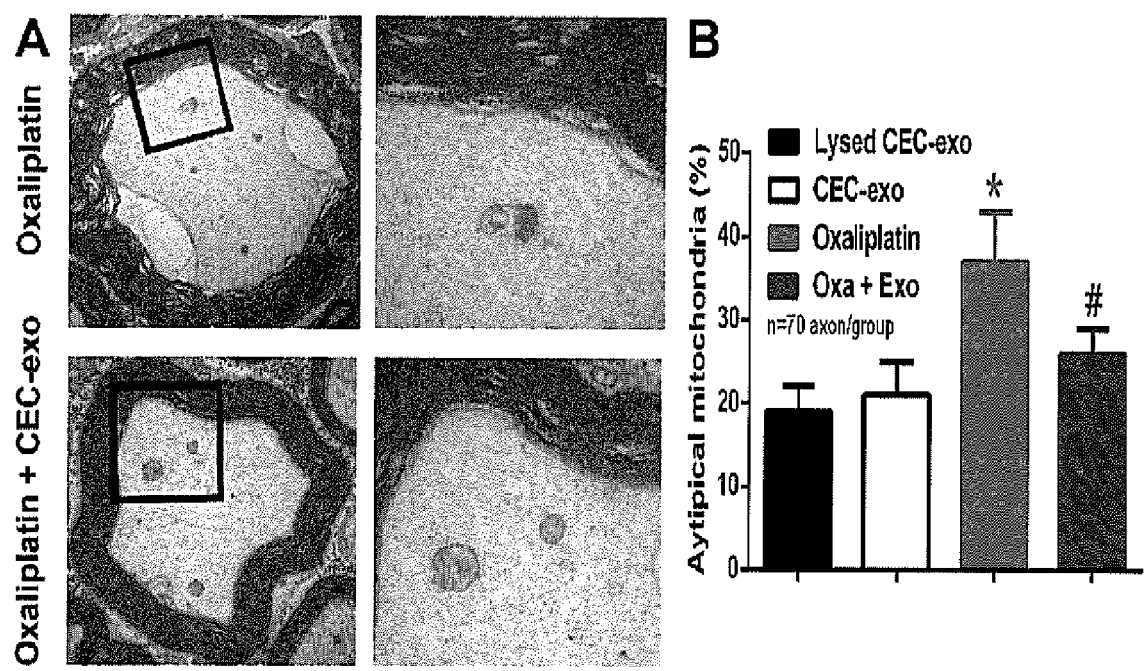
FIG. 9A depicts a transmission electron microscopy (TEM) micrographs of axonal degeneration/demyelination in the small fibers when treated with and without CEC-exosomes and oxaliplatin.
FIG. 9B depicts a bar graph representing the percentage of atypical mitochondria found in axonal sections of small fibers when treated with the four treatments described in FIG. 4.
Figure 10:
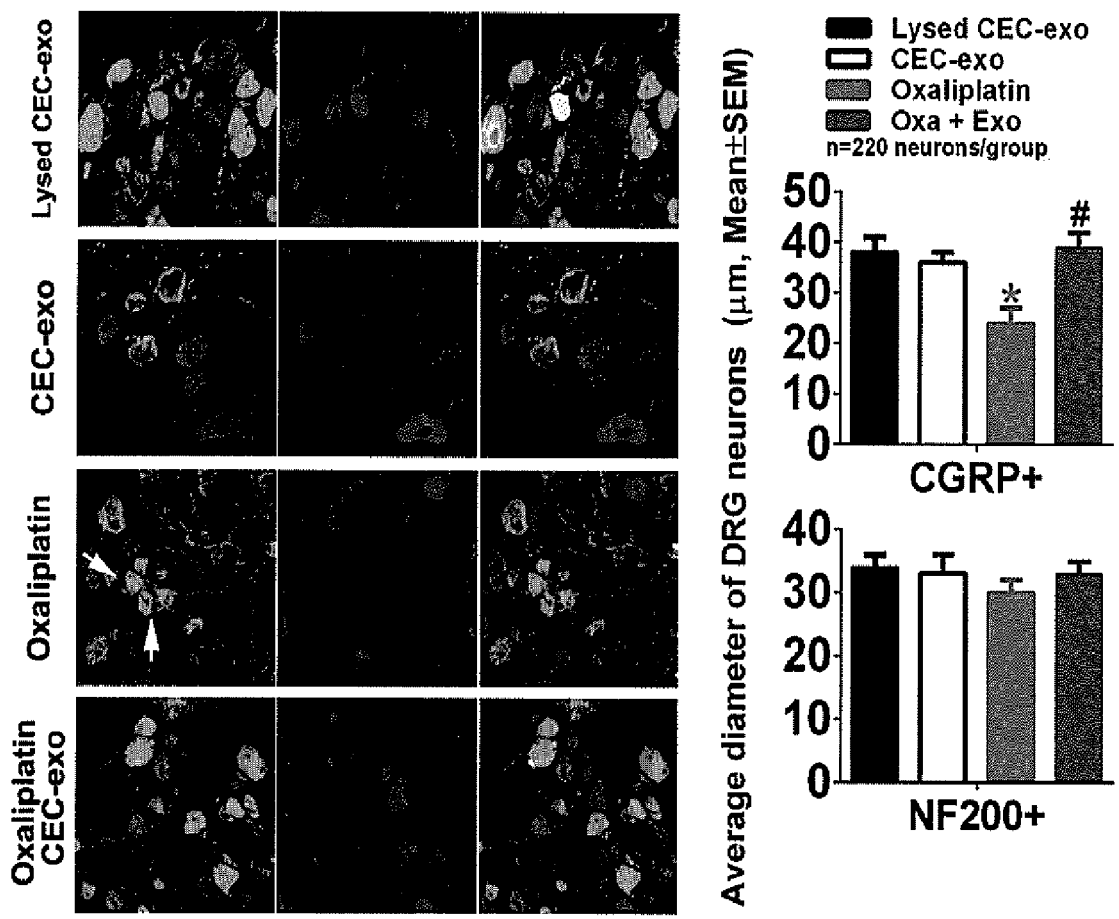
FIG. 10 depicts photomicrographs of calcitonin gene-related peptide (CGRP) DRG neurons. Double immunofluorescent analysis of DRG neurons showed that oxaliplatin selectively reduced diameters of CGRP, but not NF200 positive neurons, whereas CEC-exosomes significantly reversed CGRP neuron diameters decreased by oxaliplatin, as indicated by the bar graphs measuring the average diameter of the DRG neurons when tested for CGRP+ neurons and NF200+ neurons after treatment with the four conditions set forth in FIG. 4.

Intraepidermal nerve fibers (IENFs) are sensory nerves that innervate dermis and epidermis. Dermal tissues obtained from tumor bearing mice showed that oxaliplatin significantly reduced IEFN density assayed by the number of PGP9.5 positive fibers, which was reversed by CEC-exos (FIG. 7). Moreover, ultrastructural analysis with transmission electron microscopy (TEM) revealed that CEC-exosomes significantly reduced oxaliplatin-induced axonal degeneration/demyelination in small fibers (axon diameter <5 μm, FIG. 8) and axonal mitochondrial damage (FIG. 9A-9B). These data suggest that CEC-exosomes protect oxaliplatin-damaged terminal sensory axons and sciatic nerves that lead to peripheral neuropathy. Calcitonin gene-related peptide (CGRP) DRG neurons are primary sensory neurons encoding heat and cold perception. Double immunofluorescent analysis of DRG neurons showed that oxaliplatin selectively reduced diameters of CGRP, but not NF200 positive neurons, whereas CEC-exos significantly reversed CGRP neuron diameters decreased by oxaliplatin (FIG. 10). These data indicate that in addition to distal axons, CEC-exosomes also protect oxaliplatin-damaged DRG CGRP sensory neurons.

Figure 11:
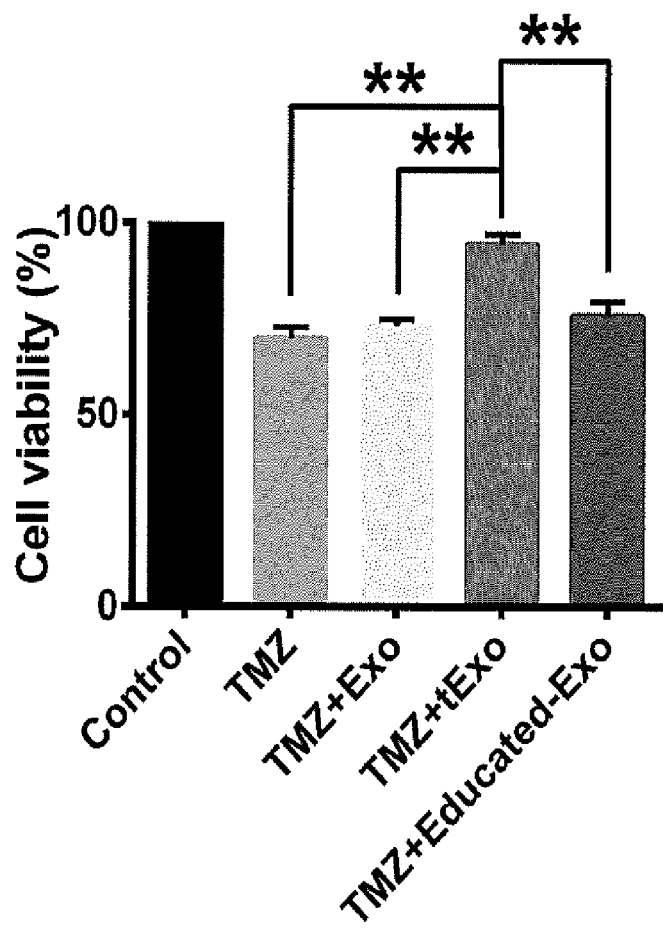
FIG. 11 depicts a bar chart depicting the percentage of cell viability loss when human glioblastoma cell line H66 were incubated with temozolomide (TMZ) in the presence of bone marrow stromal cells (MSCs) derived exosomes with and without exposure to CEC exosomes.
Figure 12A:
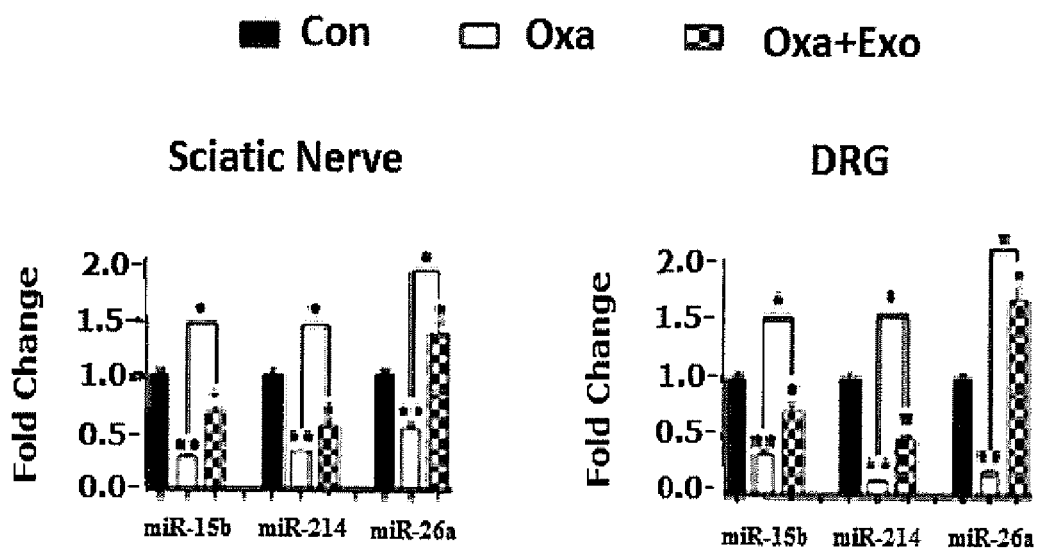
FIG. 12A depicts microRNA (miRNA) levels of miR-15b, miR-214, and miR-26a in DRG neurons and distal sciatic nerve tissues harvested from tumor-bearing mice treated with oxaliplatin and CEC-exosomes as determined using RT-PCT.
Figure 12B:
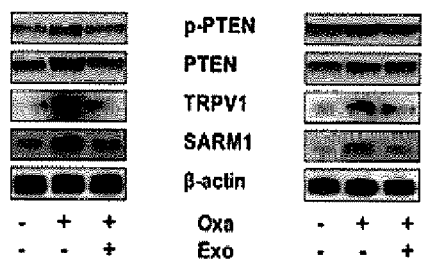
FIG. 12B depicts a Western blot depicting levels of phosphatase and tensin homolog (PTEN), sterile alpha and toll/interleukin-1 receptor motif-containing 1 (SARM1), and transient receptor potential vanilloid type 1 (TRPV1), protein levels respectively, in sciatic nerve tissues and DRG neurons from tumor-bearing mice treated with oxaliplatin and CEC-exosomes.
Figure 12C:
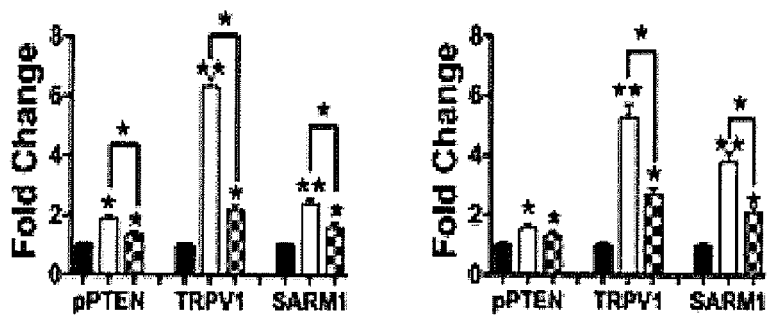
FIG. 12C depicts bar charts of mRNA levels of pTEN, TRPV1 and SARM1 in DRG neurons and distal sciatic nerve tissues harvested from tumor-bearing mice treated with oxaliplatin and CEC-exosomes as determined using RT-PCT.

In additional experiments, we investigated whether exosomes derived from bone marrow stromal cells (MSCs) mediate chemoresistance of temozolomide (TMZ) against glioblastoma and whether CEC-exosomes reduce chemoresistance of TMZ by communication with exosomes derived from MSCs (MSC-exos). Compared to non-treatment control, treatment of human glioblastoma cell line H66 with TMZ (50 μM) killed tumor cells (TMZ, FIG. 11). The addition of naïve MSC-exosomes did not affect the ability of TMZ to kill tumor cells (TMZ+Exo, FIG. 11). We then treated MSCs with TMZ and then isolated exosomes from the TMZ treated MSCs (tEXo) to then treat glioblastoma cells in the presence of TMZ. We found that the effect of TMZ on tumor cells was abolished (TMZ+tExo, FIG. 11), suggesting that MSC-derived exosomes induce chemoresistance of TMZ, However, if we treated MSCs with TMZ and CEC-exosomes and then isolated exosomes from these MSCs (Educated-Exo) to treat glioblastoma cells in the presence of TMZ. We found that these educated exosomes restored the effect of TMZ on tumor cell death (TMZ+Educated-Exo, FIG. 11). These data suggest that MSC-exosomes contribute to TMZ-induced chemoresistance and that CEC-exosomes reverse chemoresistance induced by TMZ-MSC-exosomes.

CEC-Exosomes Alter Oxaliplatin-Induced miRNA and Protein Profiles in Distal Sciatic Nerves and DRG Neurons.

Figure 13A:
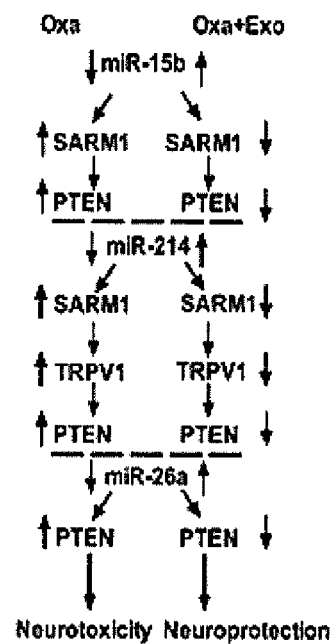
FIG. 13A depicts a schematic process chart illustrating the effects of the various factors and effect of oxaliplatin and exosomes on the ability of these factors to induce neurotoxicity and neuroprotection in vivo.
Figure 13B:
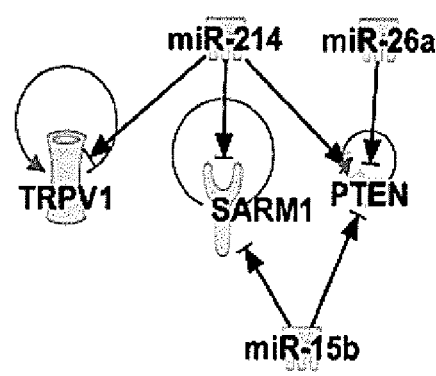
FIG. 13B depicts a schematic pathway chart illustrating the effects of the microRNAs miR-15b, miR-26a, and miR-214 with their direct target genes coding PTEN, SARM1, and TRPV1 proteins.
Figure 14A:
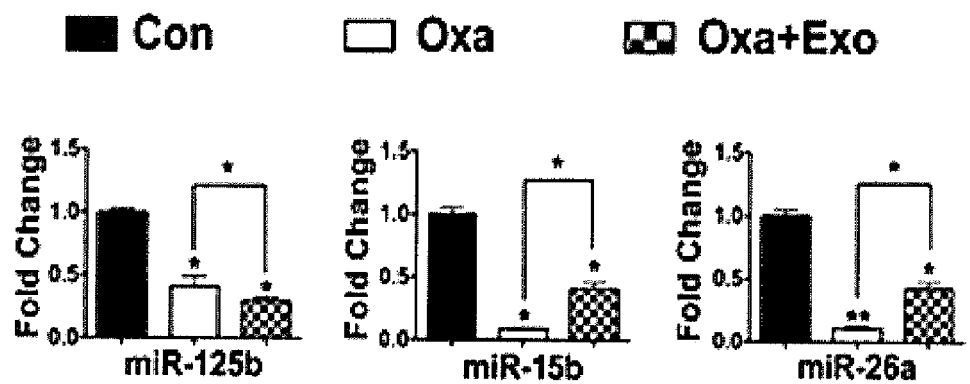
FIG. 14A depicts bar charts illustrating quantitative data of RT-PCR showing changes of miR-15b, miR-214, and miR-26a levels in sciatic nerve and DRG neurons in mice without treatment (Con), treated with oxaliplatin+lysed CEC-exosomes (Oxa), and oxaliplatin+CEC-exosomes (Oxa+Exo).
Figure 14B:
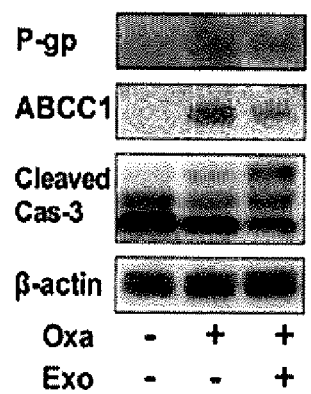
FIG. 14B depicts a Western blot photomicrograph of phosphorylated PTEN, TRPV1, and SARM1 in Con, Oxa and Oxa+Exo groups.
Figure 14C:
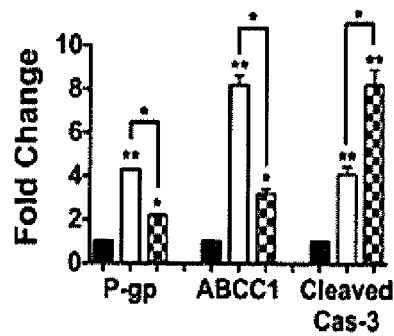
FIG. 14C depicts a bar chart quantifying the data presented in FIG. 14B of phosphorylated PTEN, TRPV1, and SARM1 in Con, Oxa and Oxa+Exosome treated groups.

To investigate potential molecular mechanisms underlying the therapeutic effect of CEC-exosome on CIPN, we analyzed microRNA (miRNA) levels and their putative target proteins in DRG neurons and distal sciatic nerve tissues harvested from tumor-bearing mice treated with oxaliplatin and CEC-exosomes. The distal sciatic nerve tissues were selected because distal sural nerve is commonly used in human diagnostic biopsies for CIPN. Quantitative RT-PCR (qRT-PCR) and Western blot analyses showed that compared to the oxaliplatin treatment, CEC-exosomes in combination with oxaliplatin significantly increased miR-15b, miR-26a, and miR-214, but substantially reduced protein levels of phosphatase and tensin homolog (PTEN), sterile alpha and toll/interleukin-1 receptor motif-containing 1 (SARM1), and transient receptor potential vanilloid type 1 (TRPV1), respectively, in sciatic nerve tissues and DRG neurons (FIGS. 12A-12C, and 13A-13B). Alteration of these protein levels by oxaliplatin or CEC-exos appears more robust in the distal sciatic nerves than in DRG neurons (FIGS. 12A-12C, and 13A-13B). These three proteins are known to mediate axonal functions and to be involved in CIPN. TRPV1 is mainly expressed in intraepidermal nerve fibers (IENFs) and increased sensitization of TRPV1 induces CIPN. Deletion of SARM1 prevents vincristine-induced CIPN by reducing loss of IENFs and distal sciatic axons. Ablation of PTEN promotes axonal growth of DRG neurons. Using Ingenuity Pathway Analysis (IPA), we found that miR-15b, miR-26a, and miR-214 form a network with their direct target genes coding PTEN, SARM1, and TRPV1 proteins (FIGS. 13A & 13B). Thus, our data of inverse levels between the miRNAs and the proteins suggest that CEC-exosomes inactivate a network of miRNAs/proteins that promote CIPN.

CEC-Exosomes Alter Oxaliplatin-Induced miRNA and Protein Profiles in Ovarian Cancer.

Chemoresistance diminishes efficacy of chemotherapeutic agents to cancer cells and the key molecular players involved in chemoresistance are primarily the ATP-dependent binding cassette (ABC) transporters such as ABCB1

Figure 15A:
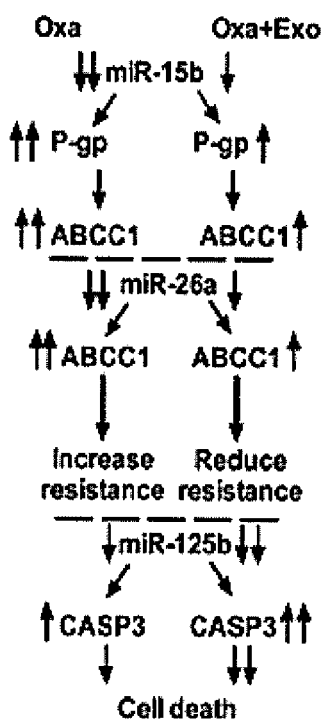
FIG. 15A depicts a schematic representation of the pathway and effect of miRNAs and their target proteins that are involved in oxaliplatin-induced neurotoxicity and in CEC-exo-induced neuroprotection.
Figure 15B:
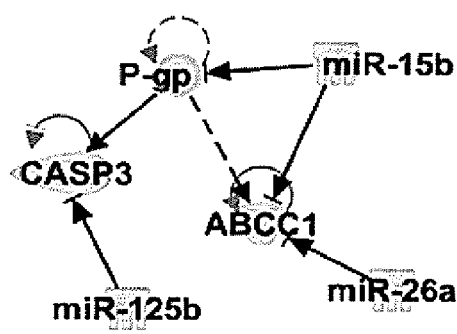
FIG. 15B depicts a graphical diagram depicting a proposed signaling network of miR-15b, -26a, and -214 and their target genes.

(P-glycoprotein, P-gp1) and ABCC1 (multidrug resistance-associated protein 1, MRP1). We analyzed miRNA levels and their putative target proteins in tumor tissues harvested from tumor-bearing mice treated with oxaliplatin and CEC-exosomes. qRT-PCR and Western blot analyses showed that oxaliplatin significantly reduced miR-15b and miR-26a, but increased protein levels of P-gp1 and ABCC1 (FIG. 14A-14C), however, CEC-exosomes in combination with oxaliplatin increased oxaliplatin-reduced miR-15b, and miR-26a, and significantly reduced oxaliplatin-increased protein levels of P-gp1 and ABCC1 (FIGS. 14A-14C and 15A-15B). Moreover, CEC-exosomes in combination with oxaliplatin further downregulated miR-125b and elevated cleaved Caspase 3 protein (FIGS. 14A-14C and 15A-15B). IPA revealed that miR-15b, miR-26a, and miR-125b form a network with their target genes coding P-gp1, ABCC1, and Caspase 3 proteins (FIG. 15A-15B). Therefore, these data suggest that CEC-exosomes regulate a network of miRNAs/proteins in tumor by suppressing oxaliplatin-induced chemoresistance genes and by amplifying oxaliplatin-induced cancer cell death, which leads to CEC-exosomal enhancement of the anti-cancer effect of platinum drugs.

The experiments performed and described herein provide ample and statistically significant findings that lead one to conclude that exosomes derived from cerebral endothelial cells mitigate neurotoxicity induced by chemotherapy and enhance the effects of chemotherapy.

While some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. This description of some embodiments should be understood to include all novel and non-obvious combinations of elements described herein, and embodiments may be presented in this or a later application to any novel and non-obvious combination of these elements. The foregoing embodiments are illustrative, and no single feature or element is essential to all possible combinations that may be claimed in this or a later application.

What is claimed is:

1. A method for preventing and/or treating chemotherapy-induced peripheral neuropathy (CIPN) caused by the administration of at least one platinum based chemotherapeutic agent in a human subject in need thereof,
    wherein the human subject will be treated with or is currently treated with a chemotherapeutic agent comprising at least one platinum agent,
    the method comprising administering a therapeutically effective amount of exosomes isolated from primary or cultured human cerebral endothelial cells intravenously to the subject.

2. The method according to claim 1, wherein the CIPN comprises the syndrome: painful CIPN.

3. The method according to claim 2, wherein the painful CIPN comprises a syndrome selected from the group consisting of: painful acute chemotherapy-induced peripheral neuropathy (painful ACIPN) and painful chronic chemotherapy-induced peripheral neuropathy (painful CCIPN).

4. The method according to claim 1, wherein the exosomes comprise the markers Alix and CD63.

5. The method according to claim 1, wherein the subject is administered about $1\times10^1$ to about $1\times10^{15}$ exosomes per kg body weight of the patient.

6. The method according to claim 5, wherein the subject is administered about $1\times10^9$ to about $1\times10^{15}$ exosomes per kg body weight of the patient.

7. The method according to claim 1, wherein the exosomes are autologous, or allogeneic.

8. The method according to claim 7, wherein the exosomes are isolated from human primary tissue cerebral endothelial cells.

9. The method according to claim 1, wherein the exosomes are first subjected to ischemic or other forms of physiological stress prior to their administration to the subject.

10. The method according to claim 1, wherein the chemotherapeutic agent is oxaliplatin.

11. The method according to claim 1, wherein the symptoms of CIPN comprise pain, tingling, numbness, problems distinguishing temperature, or any combination thereof.

* * * * *